US010782303B2

(12) United States Patent
Yeung et al.

(10) Patent No.: US 10,782,303 B2
(45) Date of Patent: Sep. 22, 2020

(54) DIAGNOSIS AND TREATMENT OF MERS-RELATED RENAL DISEASE

(71) Applicant: EMV MERS LIMITED, Tortola (VG)

(72) Inventors: Man-Lung Yeung, Hong Kong (CN); Jasper Fuk-Woo Chan, Kowloon (CN); Johnson Yiu-Lam Lau, Newport Beach, CA (US); Kwok Yung Yuen, Pokfulam (CN)

(73) Assignee: EMV Mers (HK) Limited, Central (HK)

( * ) Notice: Subject to any disclaimer, the term of this patent is extended or adjusted under 35 U.S.C. 154(b) by 76 days.

(21) Appl. No.: 15/579,528

(22) PCT Filed: Jun. 3, 2016

(86) PCT No.: PCT/US2016/035836
§ 371 (c)(1),
(2) Date: Dec. 4, 2017

(87) PCT Pub. No.: WO2016/197003
PCT Pub. Date: Dec. 8, 2016

(65) Prior Publication Data
US 2018/0149659 A1 May 31, 2018

Related U.S. Application Data

(60) Provisional application No. 62/170,780, filed on Jun. 4, 2015.

(51) Int. Cl.

| | |
|---|---|
| ***A61K 31/7105*** | (2006.01) |
| ***A61K 31/713*** | (2006.01) |
| ***A61K 31/7088*** | (2006.01) |
| ***A61P 11/00*** | (2006.01) |
| ***C12N 15/113*** | (2010.01) |
| ***G01N 33/68*** | (2006.01) |
| ***C12Q 1/6883*** | (2018.01) |
| ***C12Q 1/70*** | (2006.01) |
| ***C07K 16/22*** | (2006.01) |
| ***A61K 39/00*** | (2006.01) |

(52) U.S. Cl.
CPC ......... *G01N 33/68* (2013.01); *A61K 31/7088* (2013.01); *A61K 31/713* (2013.01); *A61K 31/7105* (2013.01); *A61K 39/00* (2013.01); *A61P 11/00* (2018.01); *C07K 16/22* (2013.01); *C12Q 1/6883* (2013.01); *C12Q 1/70* (2013.01); *C07K 2317/76* (2013.01); *C12Q 2600/112* (2013.01); *C12Q 2600/118* (2013.01); *C12Q 2600/158* (2013.01); *G01N 2333/165* (2013.01); *G01N 2333/4703* (2013.01); *G01N 2333/50* (2013.01); *G01N 2800/347* (2013.01); *G01N 2800/52* (2013.01)

(58) Field of Classification Search
None
See application file for complete search history.

(56) References Cited

FOREIGN PATENT DOCUMENTS

| | | |
|---|---|---|
| WO | 2015057942 | 4/2015 |
| WO | 2015057966 | 4/2015 |

OTHER PUBLICATIONS

Eckerle et al. Virology Journal 2013,10:359 (5 pages).*
PCT Search Report & Written Opinion dated Sep. 12, 2016 for PCT/US2016/035836 filed on Jun. 3, 2016 in the name of EMV Mers (HK) Limited.
Alghamdi, M. et al, MERS CoV Infection in Two Renal Transplant Recipients: Case Report; American Journal of Transplantation 2015; 15: 1101-1104.
Bhadra, Sanchita et al, Real-Time Sequence-Validated Loop-Mediated Isothermal Amplification Assays for Detection of Middle East Respiratory Syndrome Coronavirus (MERS-CoV); PLOS ONE; Apr. 9, 2015 (21 pages).
Eckerle, Isabella et al, In-vitro Renal Epithelial Cell Infection Reveals a Viral Kidney Tropism as a Potential Mechanism or Acute Renal Failure during Middle East Respiratory Syndrome (MERS) Coronavirus Infection; Virology Journal 2013, 10:359 (5 pages).
Lu, Xiaoyan et al, Real-Time Reverse Transcription-PCR Assay Panel for Middle East Respiratory Syndrome Coronavirus, Journal of Clinical Microbiology, Jan. 2014 vol. 52 No. 1; pp. 67-75.
Assri A., et al., "Epidemiological, Demographic, and Clinical Characteristics of 47 Cases of Middle East Respiratory Syndrome Coronavirus Disease From Saudi Arabia: a Descriptive Study", The Lancet, Jul. 26, 2013, vol. 13, pp. 752-761.
Bitzer M., et al., "A Mechanism of Suppression of TGF—β/SMAD Signaling by NF-κB/RelA", Genes and Development, 2000, vol. 14, pp. 187-197.
Chan J.F-W., et al,, "Differential Cell Line Susceptibility to the Emerging Novel Human Betacoronavirus 2c EMC/2012: Implications for Disease Pathogenesis and Clinical Manifestation", The Journal of Infectious Diseases, 2013, vol. 207, pp. 1743-1752.

(Continued)

*Primary Examiner* — Tracy Vivlemore
(74) *Attorney, Agent, or Firm* — Fish IP Law, LLP

(57) ABSTRACT

Methods for treating, diagnosing, and providing prognostic information for kidney disease related to MERS-CoV infection are described. Transcription and translation products (for example, mRNA or peptides) of FGF2, Smad7, and/or sequences upstream of FGF2 are useful as markers that indicate kidney disease and/or provide prognostic information related to the course of kidney disease related to MERS-CoV infection. Such kidney disease can be treated and/or mitigated by reducing the availability of FGF2, Smad7, and/or a sequence upstream from FGF2 by reducing and/or regulating transcription and by sequestering related peptides using a large molecule binding partner, such as an antibody. Sequences for useful siRNAs and antisense oligonucleotides are provided.

12 Claims, 15 Drawing Sheets

Specification includes a Sequence Listing.

(56) References Cited

OTHER PUBLICATIONS

Chan J.F-W. et al,, "Broad-spectrum Antivirals for the Emerging Middle East Respiratory Syndrome Coronavirus", Journal of Infection, 2013, vol. 67, pp. 606-616.

Chan J.F-W., et al:, "Is the Discovery of the Novel Human Betacoronavirus 2c EMC/2012 (HCoV-EMC) the Beginning of Another Sars-like Pandemic?", Journal of Infection, 2012, vol. 65, pp. 477-489.

Chan J.F-W., et al., The emerging novel Middle East respiratory syndrome coronavirus: The "knowns" and "unknowns", Journal of the Formosan Medical Association, 2013, vol. 112, pp. 372-381.

Chan K-H., et al., "Cross-reactive Antibodies in Convalescent Sars Patients' Sera Against the Emerging Novel Human Coronavirus Emc (2012) by Both immunofluorescent and Neutralizing Antibody Tests", Journal of Infection, 2013, vol. 67, pp. 130-140.

Cheng V.C.C., et al., "Severe Acute Respiratory Syndrome Coronavirus as an Agent of Emerging and Reemerging Ingection", Clinical Microbiology Reviews, Oct. 2007, vol. 20 (4), pp. 660-694.

Drosten C., et al., "Clinical Features and Virological Analysis of a Case of Middle East Respiratory Syndrome Coronavirus Infection", LANCET Infectious Diseases, 2013, vol. 13, pp. 745-751.

Falzarano D., et al., "Infection with MERS-CoV Causes Lethal Pneumonia in the Common Marmoset", PLOS Pathogens, Aug. 2014, vol. 10 (8), e1004250, 13 pages.

Falzarano D., et al., "Inhibition of Novel β Coronavirus Replication by a Combination of Interferon-α2b and Ribavirin", Scientific Reports, 2013, vol. 3:1686, 6 pages.

Floege J., et al., "Basic Fibroblast Growth Factor Augments Podocyte Injury and. Induces Glomerulosclerosis in Rats with Experimental Membranous Nephropathy", Journal of Clinical Investigation, Dec. 1995, vol. 96, pp. 2809-2819.

Hung I.F.N., at al., "Viral Loads in Clinical Specimens and SARS Manifestations" Emerging Infectious Diseases, Sep. 2004, vol. 10 (9), pp. 1550-1557.

Jaffar A., at al., "Ribavirin and Interferon Therapy in Patients Infected With the Middle East Respiratory Syndrome Coronavirus: an Observational Study", International Journal of Infectious Diseases, 2014, vol. 20, pp. 42-46.

Lan H.Y., et al., "Inhibition of Renal Fibrosis by Gene Transfer of Inducible Smad7 Using Ultrasound-Microbubble System in Rat UUO Model", Journal of American Society of Nephrology, 2003, vol. 14, pp. 1535-1548.

Li Z., et al., "Novel Cystogenic Role of Basic Fibroblast Growth Factor in Developing Rodent Kidneys", American Physiological Society, Renal Physiology, 2006, vol. 291, pp. F289-F296.

Lu L.. et al., "Structure-based Discovery of Middle East Respiratory Syndrome Coronavirus Fusion Inhibitor", Nature Communications, Macmillan Publishers Ltd, Jan. 28, 2014, vol. 5 (3067), pp. 1-12.

Monteleone G., "Phase I Clinical Trial of Smad7 Knockdown Using Antisense Oligonucleotide in Patients With Active Crohn's Disease", The American Society of Gene & Cell Therapy, Apr. 2012, vol. 20 (4), pp. 870-876.

Okado T., et al., "Smad7 mediates transforming growth factor-β—induced apoptosis in mesangial cells", International Society of Nephrology, Kidney International, 2002, vol. 62, pp. 1178-1186.

Peiris J.S.M., et al., "Coronavirus as a Possible Cause of Severe Acute Respiratory Syndrome", The Lancet, Apr. 19, 2003, vol. 361, pp. 1319-1325.

Peiris J.S.M., et al., "Severe Acute Respiratory Syndrome", Nature Medicine Supplement, Dec. 2004, vol. 10(12), pp. s88-s97.

Schiffer M., et al., "Apoptosis in podocytes induced by TGF-β and Smad7", The Journal of Clinical Investigation, Sep. 2001, vol. 108 (6), pp. 807-816.

Yao Y., et al,, "An Animal Model of MERS Produced by Infection of Rhesus Macaques With MERS Coronavirus", The Journal of Infectious Diseases, Jan. 15, 2014, vol. 209, pp. 236-242.

Zaki A.M., et al., "Isolation of a Novel Coronavirus from a Man with Pneumonia in Saudi Arabia", The New England Journal of Medicine, 2012, vol. 367, pp. 1814-1820.

Zhou J., et al., "Active Replication of Middle East Respiratory Syndrome Coronavirus and Aberrant Induction of Inflammatory Cytokines and Chemokines in Human Macrophages: Implications for Pathogenesis", The Journal of Infectious Diseases, 2014, vol. 209, pp, 1331-1342.

Zorzi F., et al., "A Phase 1 Open-label Trial Shows That Smad7 Antisense Oligonucleotide (GED0301) Does Not Increase the Risk of Small Bowel Strictures in Crohn's Disease", Alimentary Pharmacology and Therapeutics, 2012, vol. 36, pp. 850-857.

* cited by examiner

DIAGNOSIS AND TREATMENT OF MERS-RELATED RENAL DISEASE

This application claims the benefit of U.S. Provisional Application No. 62/170,780, filed on Jun. 4, 2015. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is diagnosis and treatment of disease and conditions associated with coronavirus infection, particularly MERS.

BACKGROUND

The background description includes information that may be useful in understanding the present invention. It is not an admission that any of the information provided herein is prior art or relevant to the presently claimed invention, or that any publication specifically or implicitly referenced is prior art.

Middle East Respiratory Syndrome Coronavirus (MERS-CoV) is a betacoronavirus thought to have originated in bats. As the name implies, human infection with MERS-CoV can result in severe human disease with acute respiratory distress syndrome (ARDS). The mode of transmission is not clear. Camels are known to harbor MERS-CoV, and both camel-to-human and human-to-human transmission have been proposed. Currently diagnosis is by a positive molecular diagnostics (for example, RT-PCR) test for two specific genomic target sequences, or molecular diagnostics identification of a single target sequence with sequencing of a second.

Infection with MERS-CoV can also result in multiorgan failure in humans[1-3], with acute renal failure as one of the major contributing factors for the high case-fatality rate associated with this virus[4-10]. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. This renal failure is a clinical feature that is not commonly associated with other coronavirus infections, such as SARS. Unfortunately, while molecular diagnostics approaches are useful for identifying the presence of the MERS-CoV virus they are not predictive or prognostic for renal involvement.

Various treatments for MERS-CoV infection have been attempted. Treatment with interferon and interferon in combination with ribavirin have been attempted, but results have been mixed. Inhibition of viral protease has also been proposed. Unfortunately the pathogenic mechanism for renal damage associated with MERS infection, which is a significant contributor to mortality, is unknown and thus not readily amenable to specific treatment.

Thus, there is still a need for methods and compositions that provide diagnosis and/or prognosis of renal failure related to MERS-CoV infection and for treatment of such renal failure.

SUMMARY OF THE INVENTION

The inventive subject matter provides methods for treating, diagnosing, and providing prognostic information for kidney disease related to MERS-CoV infection. Transcription and translation products (for example, mRNA or peptides) of FGF2, Smad7, and/or sequences upstream of FGF2 are useful as markers that indicate kidney disease and/or provide prognostic information related to the course of kidney disease related to MERS-CoV infection. Such kidney disease can be treated and/or mitigated by reducing the availability of FGF2, Smad7, and/or a sequence upstream from FGF2 by reducing and/or regulating transcription and by sequestering related peptides using a large molecule binding partner, such as an antibody.

One embodiment of the inventive concept is a method of diagnosing renal disease associated with MERS-CoV infection by obtaining a sample from an individual suspected of being infected with MERS-CoV, characterizing expression of at least one of one or more of FGF2, Smad7, and a sequence upstream of FGF2 and identifying over-expression of at least one of such a marker(s), where such over-expression indicates renal disease associated with MERS-CoV infection. In some embodiments over-expression can be determined using an RNA transcript, for example by RT-PCR. In other embodiments a polypeptide of one or more of FGF2, Smad7, and a sequence upstream of FGF2 is characterized, for example using an immunoassay.

Another embodiment of the inventive concept is a method of obtaining prognostic information related to renal disease associated with MERS-CoV infection by obtaining a sample from an individual suspected of being infected with MERS-CoV, characterizing expression of at least one of one or more of FGF2, Smad7, and a sequence upstream of FGF2 and identifying over-expression of at least one of such a marker(s), where such over-expression indicates renal disease associated with MERS-CoV infection. In some embodiments over-expression can be determined using an RNA transcript, for example by RT-PCR. In other embodiments a polypeptide of one or more of FGF2, Smad7, and a sequence upstream of FGF2 is characterized, for example using an immunoassay. In some embodiments such prognostic information is related to a stage of renal disease. In other embodiments the prognostic information is related to an outcome of renal disease.

Another embodiments of the inventive concept method of preventing renal disease associated with MERS-CoV infection by reducing the availability of at least one of one or more of FGF2, Smad7, and/or a sequence upstream of FGF2 in an individual infected with MERS-CoV. Such a reduction in availability is achieved by reducing gene expression and/or reducing the bioavailability of a gene product. In some embodiments the expression a gene associated with one or more of FGF2, Smad7, and/or a sequence upstream of FGF2 is reduced, for example by administration of a polynucleotide that interferes with transcription and/or translation (such as an siRNA, RNAi, ribozyme, and/or antisense polynucleotide. In other embodiments a compound (for example, a polynucleotide, a peptide, a protein, a transcription factor, and/or a small molecule) is administered that interacts with a regulatory element upstream of one or more of a gene(s) encoding FGF2, Smad7, and/or a sequence upstream of FGF2. In other embodiments a compound (such as a peptide, a protein, and/or a small molecule is administered that interacts with one or more regulatory pathway(s) associated with FGF2, Smad7, and/or a sequence upstream of FGF2. In another embodiment bioavailability is reduced by administering a binding partner (such as an antibody, a synthetic antibody, a single chain antibody, a receptor, and/or an aptamer) that has an affinity for a polypeptide corresponding to FGF2, Smad7, and a sequence upstream of FGF2.

Another embodiment of the inventive concept is a method of treating renal disease associated with MERS-CoV infection by reducing the availability of one or more of FGF2, Smad7, and/or a sequence upstream of FGF2 in an individual infected with MERS-CoV. Such a a reduction of availability is achieved by reducing gene expression and/or reducing bioavailability of a product of expression of a gene associated with one or more of FGF2, Smad7, and/or a sequence upstream of FGF2. In some embodiments the expression a gene associated with one or more of FGF2, Smad7, and/or a sequence upstream of FGF2 is reduced, for example by administration of a polynucleotide that interferes with transcription and/or translation (such as an siRNA, RNAi, ribozyme, and/or antisense polynucleotide. In other embodiments a compound (for example, a polynucleotide, a peptide, a protein, a transcription factor, and/or a small molecule) is administered that interacts with a regulatory element upstream of one or more of a gene(s) encoding FGF2, Smad7, and/or a sequence upstream of FGF2. In other embodiments a compound (such as a peptide, a protein, and/or a small molecule is administered that interacts with one or more regulatory pathway(s) associated with FGF2, Smad7, and/or a sequence upstream of FGF2. In another embodiment bioavailability is reduced by administering a binding partner (such as an antibody, a synthetic antibody, a single chain antibody, a receptor, and/or an aptamer) that has an affinity for a polypeptide corresponding to FGF2, Smad7, and a sequence upstream of FGF2.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 3C shows results from cell lysates. FIG. 3D shows results from culture media. Replication is thought to be reduced by inhibition of cell apoptosis, a process which facilitates release and spread of the virus.

DETAILED DESCRIPTION

Figure 1A:
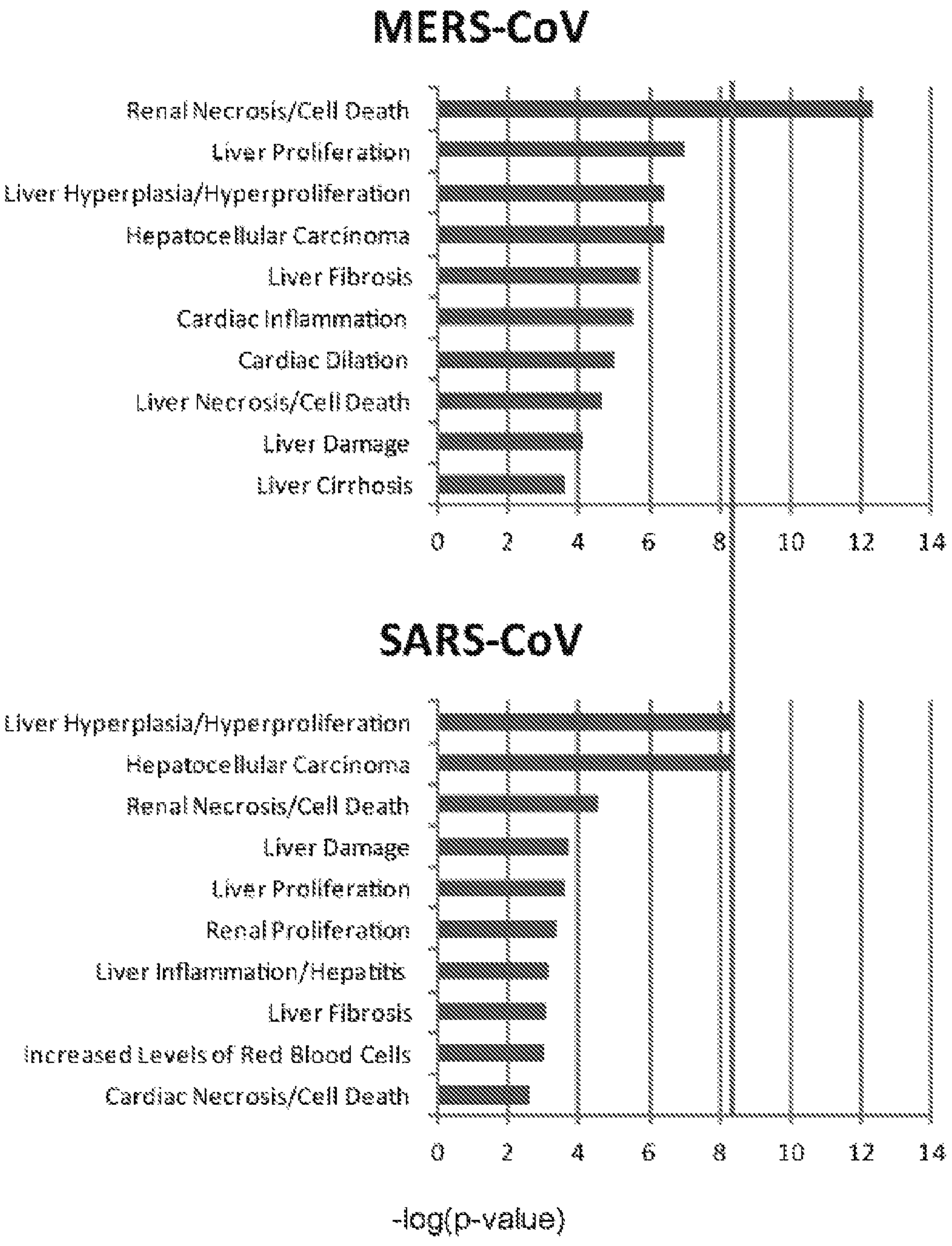
FIG. 1A shows expression levels for genes of various gene families in Calu3 cells infected with MERS-CoV and in Calu3 cells infected with SARS=CoV.

The following description includes information that may be useful in understanding the present invention. It is not an admission that any of the information provided herein is prior art or relevant to the presently claimed invention, or that any publication specifically or implicitly referenced is prior art.

The inventive subject matter provides apparatus, systems and methods in which methods and compositions are provided in which characterization the expression of FGF2, Smad7, and/or sequences upstream from FGF2 is utilized in the diagnosis and/or evaluation of the prognosis of MERS-related kidney disease, where overexpression is associated with renal and/or pulmonary disease. In other embodiments of the inventive concept inhibition of the expression and/or activity of FGF2 and/or Smad7 is(are) utilized for treatment and/or prevention of renal and/or pulmonary disease resulting from infection with MERs coronavirus.

One should appreciate that the disclosed techniques provide many advantageous technical effects, including identification of a therapeutic modality that is effective in preventing illness and/or death due to apoptotic activity in kidney cells following MERS infection. Moreover, as the inventors observed similar mechanisms in lung cells, it is contemplated that lung damage due to MERS viruses may also be reduced or even eliminated.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

One embodiment of the inventive concept includes methods useful in identifying diagnostic and/or therapeutic targets for renal and/or pulmonary disease due to MERS coronavirus infection. In such embodiments the transcription patterns of proteins in MERS-infected cells are characterized to identify proteins/peptides and/or families of proteins/peptides that can be used to predict, diagnose, mitigate, and/or prevent the kidney-damaging effects of MERS infection. In order to characterize host response to MERS-CoV infection, the transcriptomic profiles of polarized human bronchial epithelial Calu-3 cells infected with MERS-CoV can be compared to those of cells from the same cell line that are infected with severe acute respiratory syndrome coronavirus (SARS-CoV). Typical results of such studies are shown in FIG. 1A. As shown, gene expression levels of the virus-infected samples at various time points are first compared with those of the same samples at time zero (i.e. prior to infection). Typically the number of differentially expressed genes increases over time. In the exemplary data shown, for example, there were 462, 639, 1650 and 4287 differentially expressed genes observed at 2, 4, 12 and 24 hours after MERS-CoV infection, respectively. Surprisingly, genes classified under as related to renal necrosis/cell death were predominantly affected in MERS-CoV infected cells, but not in SARS-CoV-infected cells. The inventors contemplate that such results are related to the clinical observation of a high incidence of renal failure found in MERS infection that is not found in SARS-CoV-infected patients.

Although detection of MERS-CoV RNA in the urine of infected patients has been reported, direct in vivo evidence of MERS-CoV infection of the kidneys has not previously been reported. One embodiment of the inventive concept is ex vivo human kidney culture model for characterization of the effects of infection with a virus (for example, a coronavirus). In some such embodiments the coronavirus is a MERS coronavirus. The inventors contemplate that other human organ cultures (for example, human lung cultures) can also serve as models for human infection with cornaviruses (for example, a SARS coronavirus strain and/or a MERS coronavirus strain). Embodiments of the inventive concept using human kidney culture demonstrate that kidney cells in such a culture can be readily infected by MERS-CoV. This is shown in the lower panel of FIG. 1B, which shows the results of immunohistochemistry studies directed towards viral nucleocapsid proteins (NP) in such cells. To identify specific infected cell types, co-immunostaining of the infected kidney tissue for NP and various kidney cellular markers can be performed. Typically, co-localization of MERS-CoV NP with synaptopodin, CD31 and cytokeratin 18 is observed, indicating that multiple types of kidney cells including renal epithelial cells, parietal cells of Bowman's capsules, renal tubular cells, and blood vessel endothelial cells are susceptible to MERS-CoV infection. The presence of virions within the infected kidney cells can be further confirmed by electron microscopy (typical results are shown in FIG. 1C). Viral susceptibility can also be demonstrated in renal cellular models, including primary normal human mesangial cells (NHMC), podocytes and renal proximal tubular HK2 cells (FIG. 1D). Such cultures advantageously permit characterization of the biological changes induced by MERS-CoV infection in vitro.

More particularly, FIGS. 1A to 1D depict the results of ex vivo and in vitro studies characterizing infection of cells in culture to infection with MERS-CoV. FIG. 1A shows pathway analyses of MERS-CoV-infected (Top panel) and SARS-CoV-infected (bottom panel) Calu-3 cells (derived from a human lung adenocarcinoma) using differential gene expression profiles determined from such infected cells. Characterized genes are grouped into categories based on association with various clinical conditions. As shown, the patterns observed for MERS coronavirus (MERS-CoV) infection and SARS coronavirus (SARS-CoV) infection are similar, with the exception of an indication of selective overexpression of genes associated with renal necrosis in cells infected with MERS-CoV.

Figure 1B:
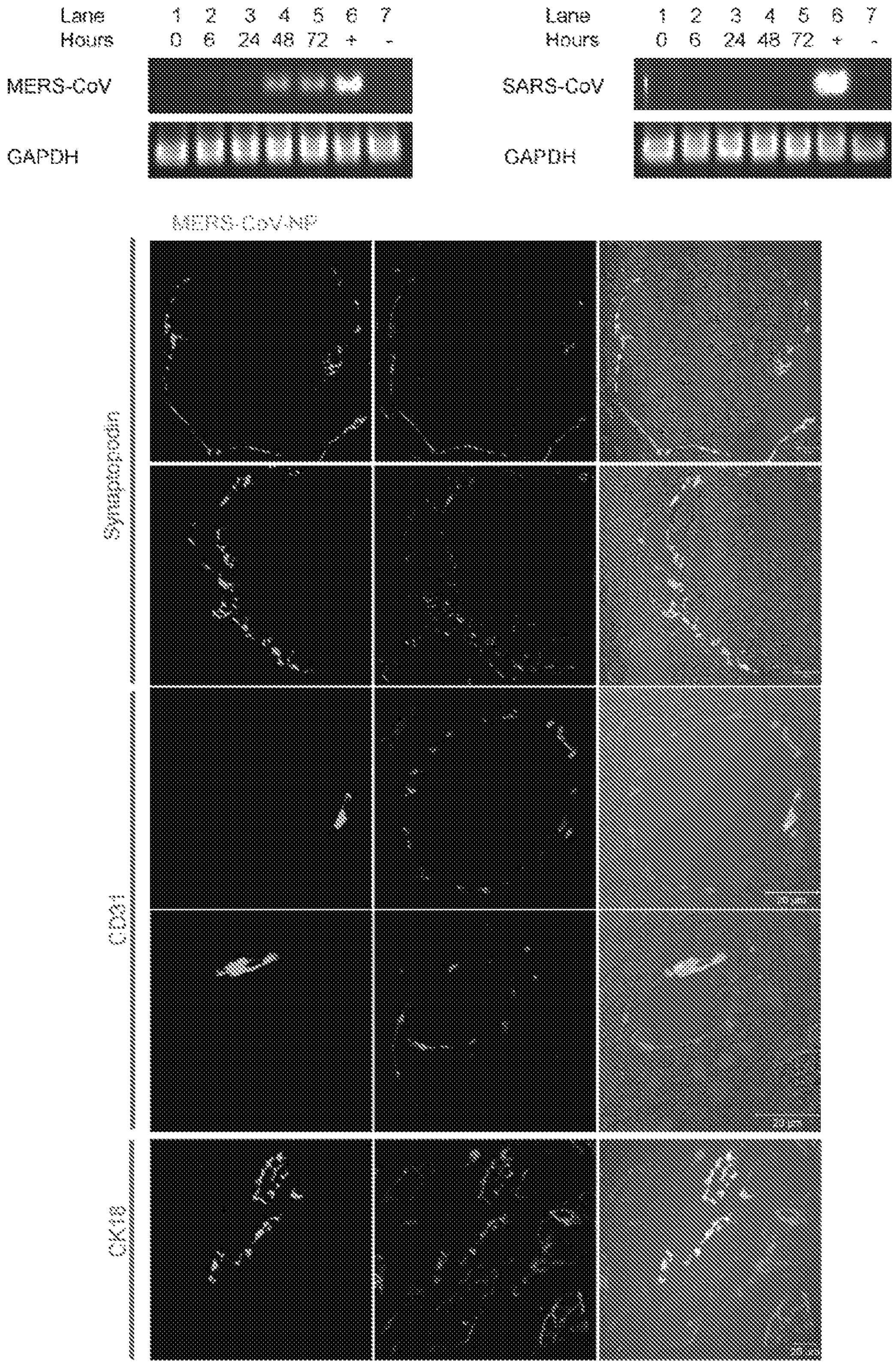
FIG. 1B shows the degree of viral RNA expression in ex vivo cultured kidney tissue infected with MERS-CoV and with SARS-CoV in the upper panel. The lower panel of FIG. 1B shows the result of immunohistochemistry studies of MERS-CoV infected kidney tissue sections, stained with antibodies directed to MERS-CoV nucleocapsid protein and cell-specific markers
Figure 1C:
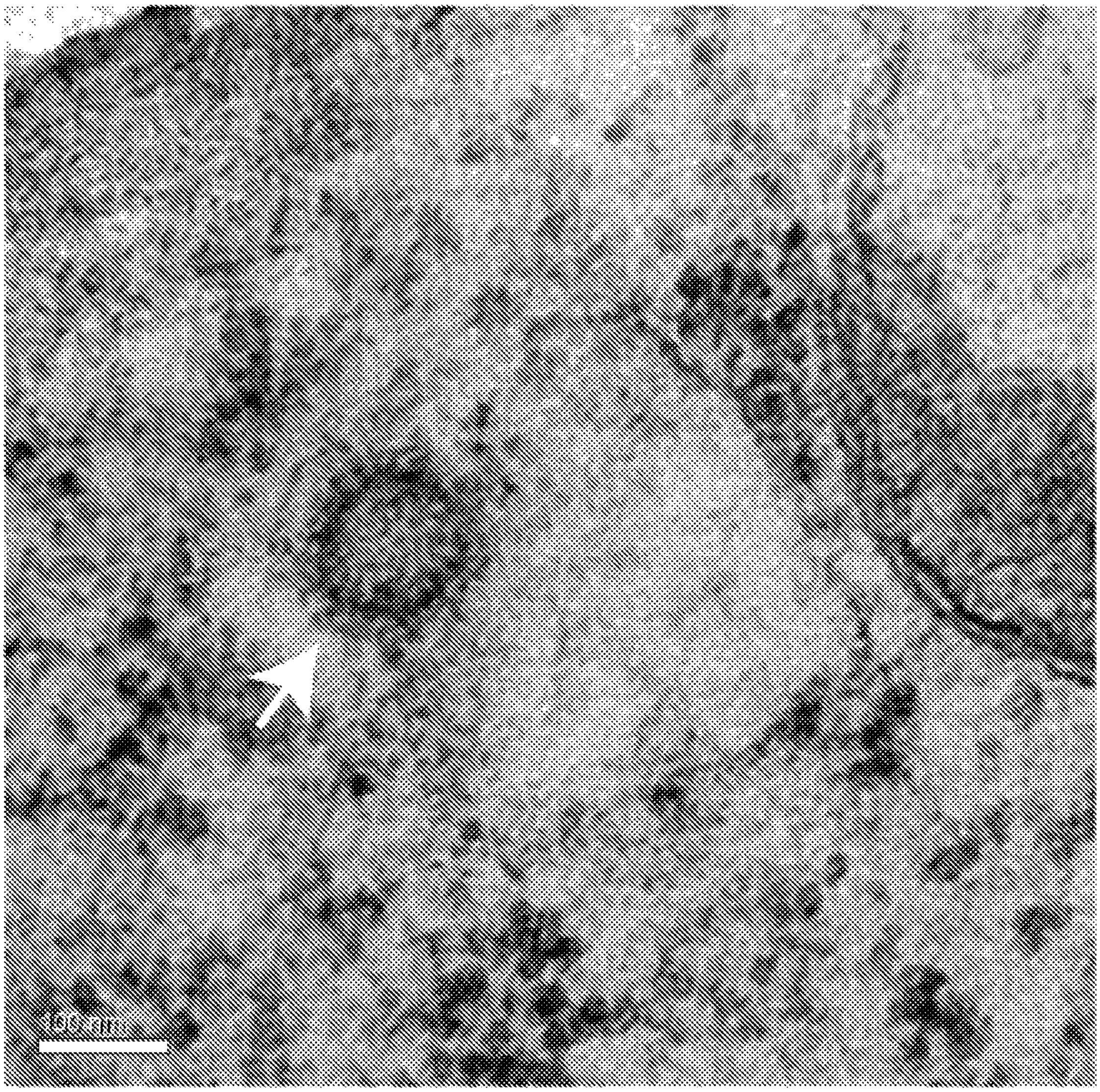
FIG. 1C is an electron micrograph of a tissue section of a MERS-CoV infected kidney, showing a viral particle in situ.
Figure 1D:
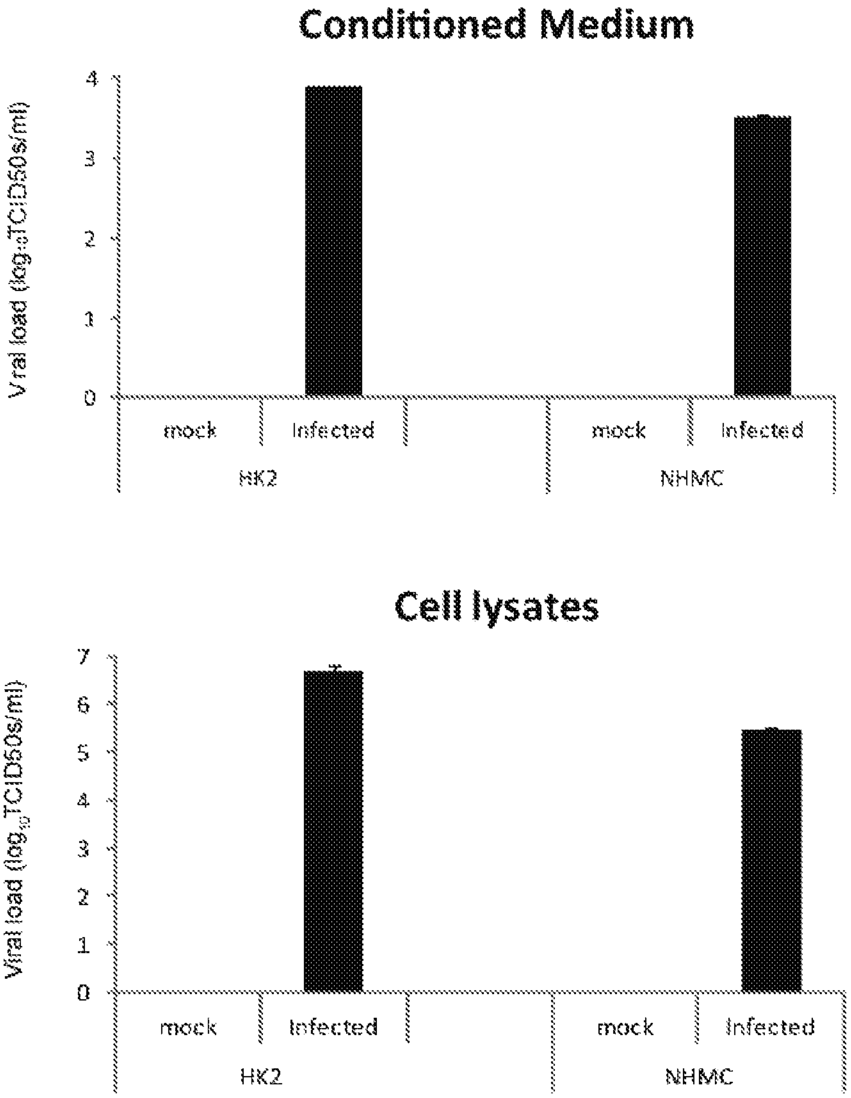
FIG. 1D shows the result of infection of HK2 cells in culture with MERS-CoV, showing release of infective MERS-CoV into the culture media (upper panel) and growth of infective MERS-CoV within the cells (lower panel).

The upper panel FIG. 1B shows results of studies in which ex vivo cultured human kidneys were inoculated with MERS-CoV (left) and with SARS-CoV (right). Total RNAs were harvested from such cells at the indicated time points after infection with MERS-CoV by inoculation. (left; lanes 1-5) and with SARS-CoV by inoculation (right; lanes 1-5). Viral RNAs were subsequently amplified using RT-PCR. MERS-CoV-infected HK2 (left; "+"; lane 6) and SARS-CoV-infected Calu-3 samples (right; "+"; lane 6) were included as positive controls. Mock-treated HK2 (left; "–"; lane 7) and Calu-3 (right; "–"; lane 7) samples were included as negative controls. The amount of constitutively expressed glyceraldehyde 3-phosphate dehydrogenase (GAPDH) mRNA present is also shown. As shown, infection of cells of cultured human kidneys with MERS-CoV results in a time-dependent increase in viral RNA that is not found in SARS-CoV infection, indicating kidney-specific effects.

The lower panels of FIG. 1B shows the results of immunohistochemistry studies of MERS-CoV infected kidneys. In a typical study MERS-CoV-inoculated human kidneys were cryosectioned and nucleoproteins (NP) of MERS-CoV were identified by immunostaining using specific antibodies by specific antibodies (left panels) labeled (either directly or indirectly via anti-species antibodies) with a first fluorescent dye. In order to identify the distribution of various cell types within such MERS-CoV infected kidneys the cryosections were co-stained with cell-type specific antibodies against synaptopodin, CD31, and/or cytokeratin 18 (CK18) (middle panels) labeled either directly or indirectly with a second dye. Co-localization of viral antigens with cellular markers is shown in the right-hand panels). FIG. 1C shows typical results from similar studies that utilize electron microscopic examination of MERS-CoV infected human kidney to provide direct identification of MERS-CoV virions in kidney tissue. The arrow indicates a MERS-CoV particle within the matrix of human kidney tissue. Such studies indicate that such human kidney cultures can be utilized as tools for identification of genetic and/or protein/peptide markers useful in indicating infection of kidneys in human patients by MERS-CoV.

Another embodiment of the inventive concept is the use of cultured cells derived from kidneys in characterization of genetic and protein/peptide markers associated with MERS-CoV infection and the prognosis of such an infection. FIG. 1D shows the results of studies in which conditioned media (top) and cell lysates (bottom) of the MERS-CoV-infected HK2 (a line of human proximal tubule epithelial cells) and NHMC (normal human mesangial cells) were exposed to MERS-CoV. Following infection the MERS-CoV content of media conditioned by such cells (top panel) and cell lysates (bottom panel) were characterized and quantified using $TCID_{50}$ assays. As shown, the quantity of MERS-CoV associated with these cultured cells indicates that cultured kidney cells are readily infected by MERS-CoV, and can be utilized as tools for identification of genetic and/or protein/peptide markers useful in indicating infection of kidneys in human patients by MERS-CoV.

Figure 2A:
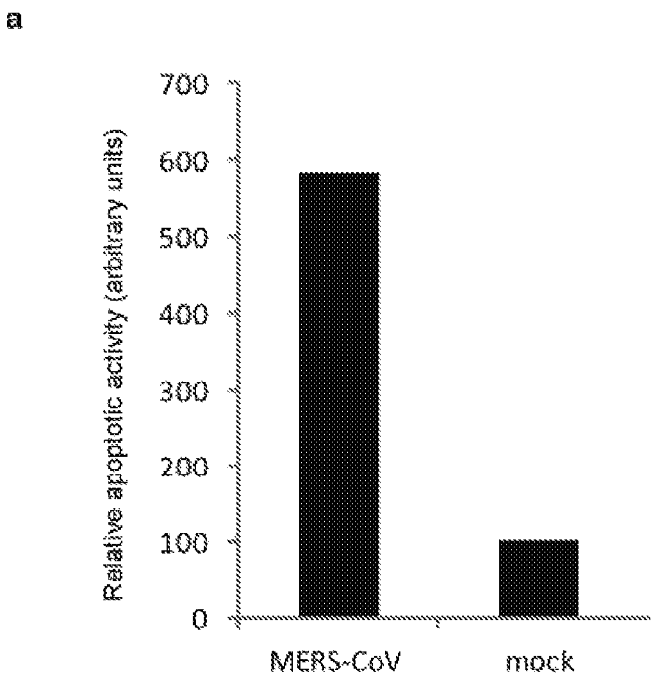
FIG. 2A depicts the results of characterization of apoptic activity in MERS-CoV infected HK2 cells.
Figure 2B:
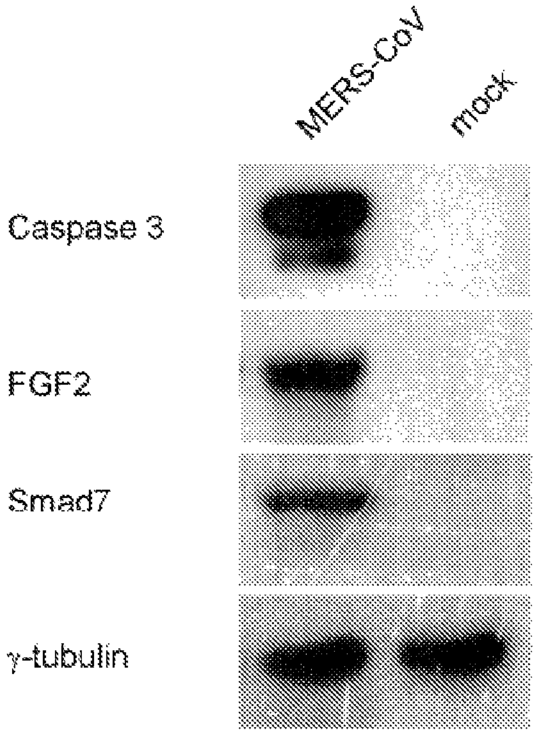
FIG. 2B shows the results of Western blot studies of HK2 cells infected with MERS-CoV. Blots were visualized using antibodies directed to Caspase 3 (an apoptosis marker) as well as FGF2 and Smad7.
Figure 2C:
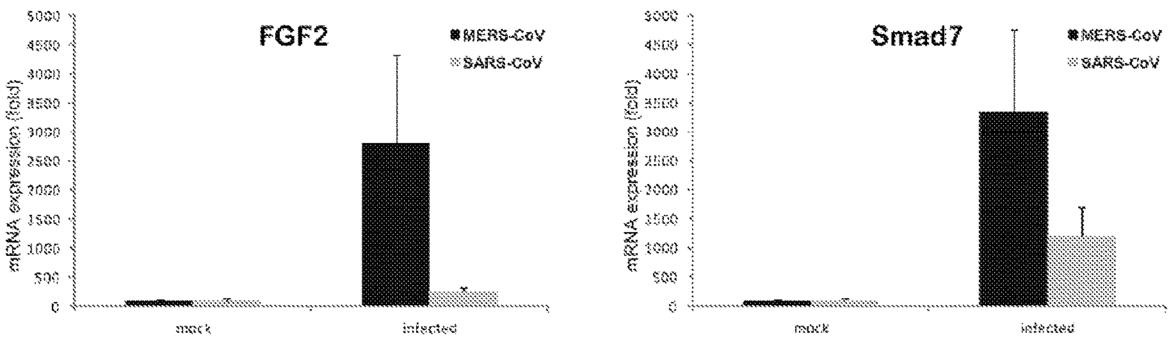
FIG. 2C and FIG. 2F show the results of characterization of FGF2 and Smad7 mRNA levels in MERS-CoV and SARS-CoV HK2 cells.
Figure 2D:
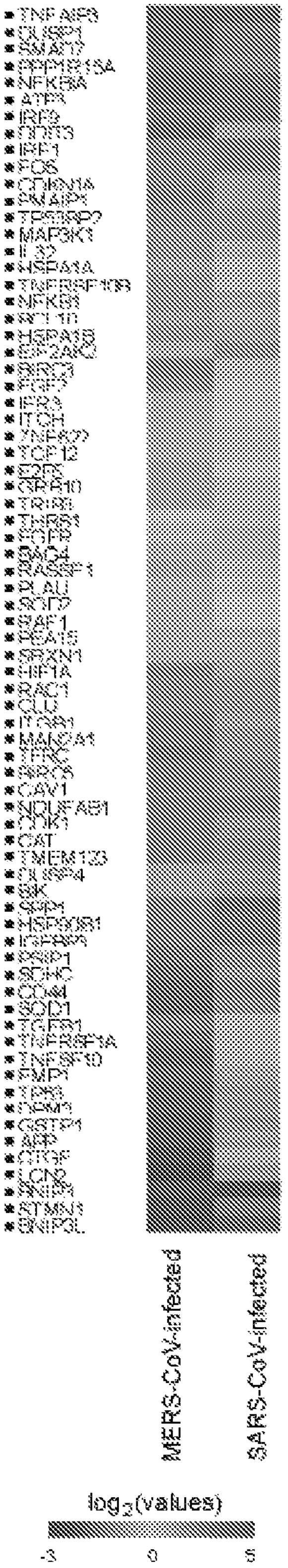
FIG. 2D is a heat map portraying mRNA expression levels in Calu3 cells infected with either MERS-CoV or SARS-CoV, for a number of markers.

Another embodiment of the inventive concept is the use of markers associated with apoptosis in the diagnosis and/or estimation of the prognosis of kidney disease in an individual with a MERS-CoV infection. Based on findings in transcriptomic and ex vivo studies, the inventors hypothesize that MERS-CoV induce renal failure through the induction of apoptosis, a major form of cell death. Presence of cellular proteins typical of apoptosis can be determined utilizing an immunological assay or staining method. FIG. 2A shows typical results for such studies in HK2 cells infected with MERS-CoV. As shown, fluorometric immunostaining assays for apoptotic caspase-3 shows strong typical pro-apoptotic responses in MERS-CoV-infected HK2 cells. The elevated expression of caspase-3 in MERS-CoV infected cells. which is not found in mock-infected cells, can be determined and/or additionally confirmed by Western blot analysis, as shown in FIG. 2B. Similar results are shown in FIG. 2B, such a test system indicates selective expression of high levels of caspase 3, FGF2, and Smad7 in MERS-CoV cells. Tubulin serves as a positive control that is highly expressed in both MERS-CoV infected cells and mock-infected cells. Similarly, quantitative studies show elevated expression of FGF2 protein in MERS-CoV infected cells (see FIG. 2E). Similar results can be demonstrated for mRNAs related to such markers. As shown in FIG. 2C and FIG. 2F, mRNA levels for FGF2 and Smad7 are selectively elevated in MERS-CoV infected HK2 cells, and not in SARS-CoV infected HK2 cells. In some embodiments of the inventive concept, elevated expression of proteins and/or mRNAs of markers identified by MERS-CoV infection of such test systems (such as Caspase-3, FGF2, and/or Smad7) or of sequences upstream from regions encoding such markers, can be used in the diagnosis or estimation of a prognosis of kidney disease associated with MERS-CoV infection.

As shown above, transcriptomic data indicates that the biological pathways related to renal necrosis/cell death are severely perturbed in MERS-CoV-infected cells (see FIG. 1A). In some embodiments of the inventive concept genes coding for FGF2 and Smad7 can be utilized as indicators of MERS-CoV-induced apoptosis (see FIG. 2C and FIG. 2D). FIG. 2D shows typical results of quantitative studies of a wide range of specific gene products in Calu-3 cells infected with MERS-CoV and in Calu-3 cells infected with SARS-CoV. Results are displayed as a heat map. Surprisingly, the inventors have identified elevated expression of both FGF2 and Smad7 in MERS-CoV-induced apoptosis in not only kidneys but also in lungs, as indicated by their elevated expression in both MERS-CoV-infected HK2 (FIGS. 2B and 2F) as well as Calu-3 cells (FIG. 2D).

Figure 2E:
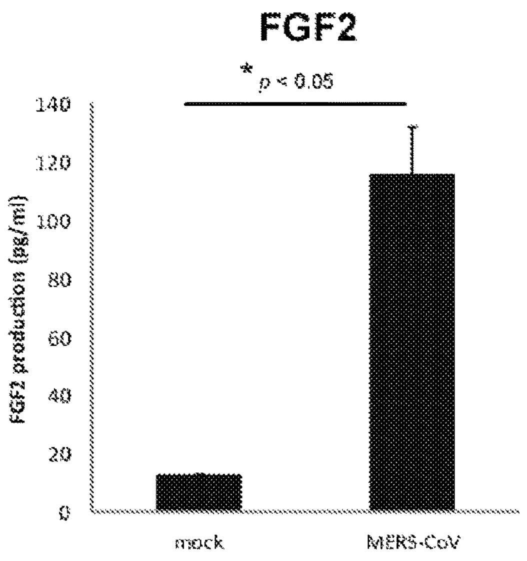
FIG. 2E shows the results of quantitative studies of the concentration of FGF2 protein produced by MERS-CoV infected cells.
Figure 2F:
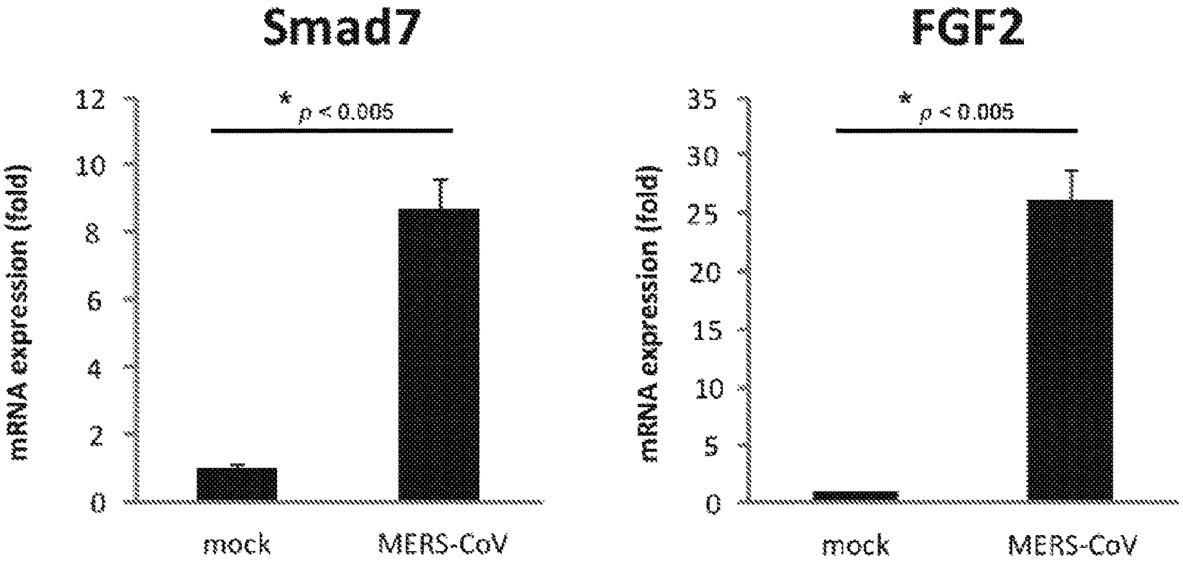

More particularly, FIGS. 2A to 2F show the results of studies of MERS-CoV infection induced the expression of FGF2 and Smad7. FIG. 2A shows the results of studies in which apoptosis of MERS-CoV-infected HK2 cells was measured by fluorometric analysis of caspase-3 activity (lane 1). Mock-infected (lane 2) cells were included as negative control. FIG. 2B depicts Western blot analysis of caspase-3, FGF2 and Smad7 in MERS-CoV- and mock-infected HK2 cells. γ-tubulin was also detected as a loading control. FIG. 2C shows MERS-CoV induction of FGF2 and Smad7 expression in lung cells. The relative expression levels of FGF2 and Smad7 in MERS-CoV- and SARS-CoV-infected Calu-3 were quantified by qPCR. FIG. 2D provides a heat map showing the candidate genes in the category of "renal necrosis/cell death" identified in FIG. 1A. FIG. 2E shows the results of studies in which quantitative measurements of secreted FGF2 were performed using an anti-FGF2 ELISA kit. FIG. 2F shows the results of studies in which the relative expression of Smad7 and FGF2 mRNA was measured using RT-qPCR (right panel). Statistical significance was evaluated by Student's t test and the ranges of p values were indicated.

In some embodiments of the inventive concept of reduction of the expression and/or functionality of proteins identified by the transcriptomic approach is utilized as a therapeutic modality in the treatment of MERS infection. The identification of Smad7 and FGF2 as mediators of MERS-CoV pathogenesis indicates that either or both can serve as therapeutic targets. It is notable that Smad7 is located upstream of FGF2, and in some embodiments sequences upstream of FGF2 are utilized as therapeutic targets. Similarly, indications of over-expression of Smad7 and/or FGF2 can serve as diagnostic and/or prognostic indicators of the presence and/or extent of renal and/or pulmonary disease associated with MERS-CoV infection. The inventors have found that compromising Smad7 and expression can subvert MERS virus-induced damage. In one embodiment expression of such apoptosis associated proteins can be reduced using siRNA. Typical results in HK2 cells show that reduction of expression can be accomplished using siRNAs against such markers (e.g. siSmad7-1 (SEQ ID NO. XXX) and siSmad7-2 (SEQ ID NO. YYY)). In such studies the expression of Smad7 was typically reduced by 75% and 40% ($p<0.05$) at protein (FIG. 3A; left top panel) and RNA levels (FIG. 3A; left bottom panel), respectively. It is contemplated that Smad7 and FGF2 expression or functionality can be reduced by other methods, including the use of RNAi, antisense polynucleotides, ribozymes, aptamers, regulatory peptides, small molecule inhibitors or analogs of regulatory factors, antibodies (natural and synthetic), and/or antibody fragments.

Figure 3A:
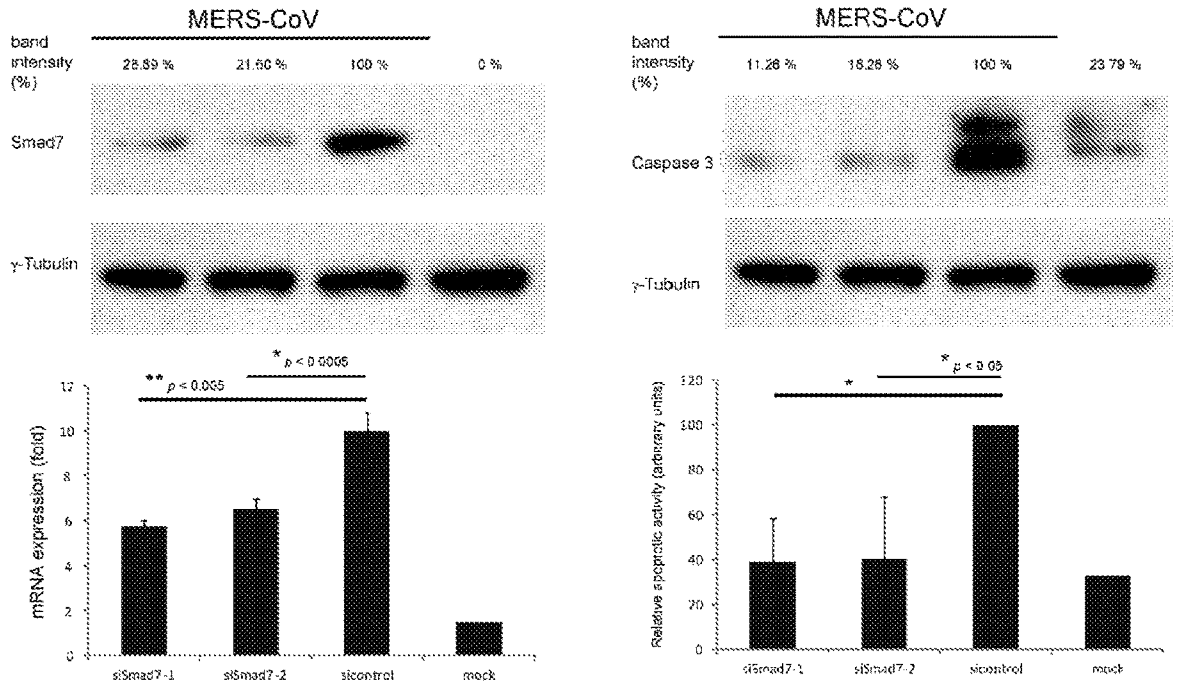
FIG. 3A shows the effect of silencing RNA (siRNAs) directed to Smad7 on MERS-CoV infected cells. As shown on the left, the degree of Smad7 mRNA expression is suppressed in siRNA treated, infected cells. As shown on the right, treatment with siRNA directed towards Smad7 suppresses expression of caspase 3 and relative apoptic activity in MERS-CoV infected cells.
Figure 3B:
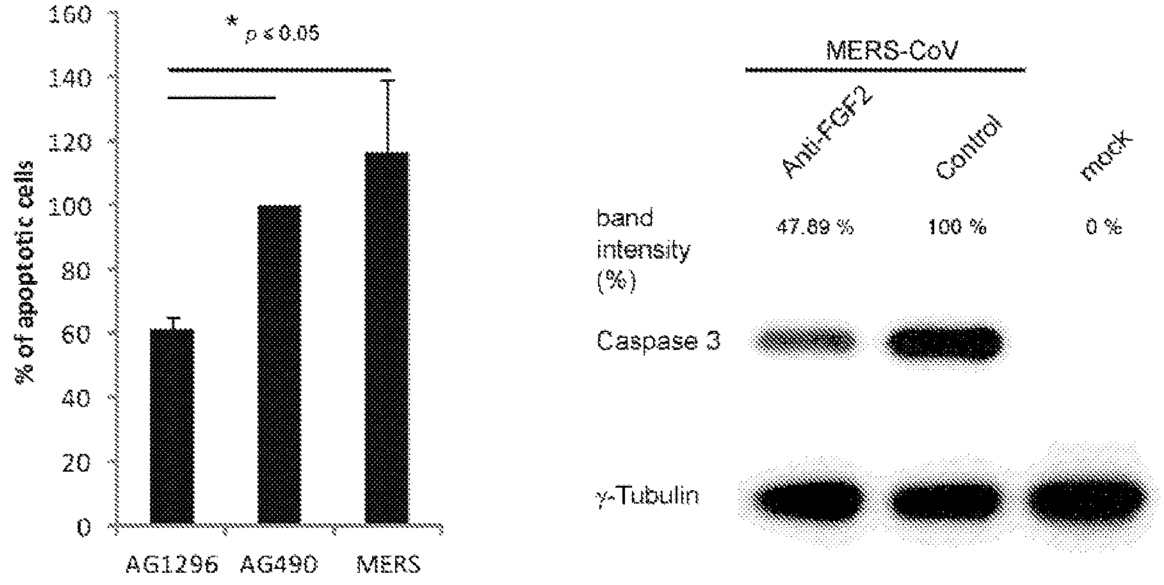
FIG. 3B shows the effect of inhibition or sequestration of FGF2 on apoptic activity in MERS-CoV infected cells. The left panel shows the effect of treatment with a small molecule inhibitor of FGF2 signaling, AG1296. The right panel shows the effect of sequestration of FGF2 with antibody directed to FGF2.
Figure 3C:
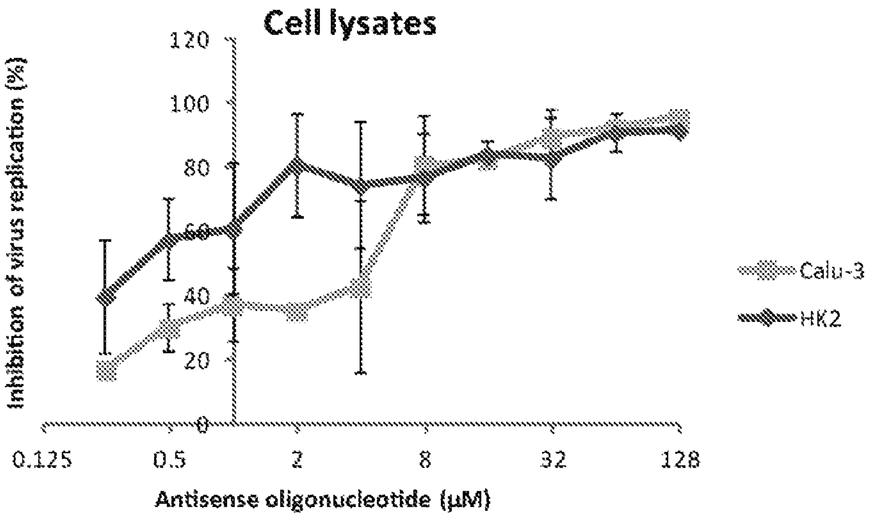
FIGS. 3C and 3D show inhibition of MERS-CoV replication by application of a Smad7 antisense oligonucleotides.
Figure 3D:
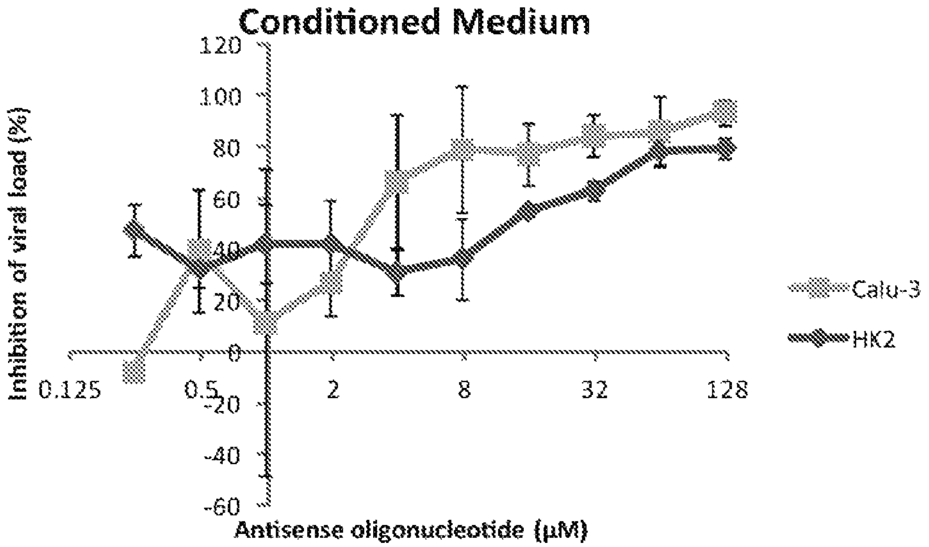
Figure 3E:
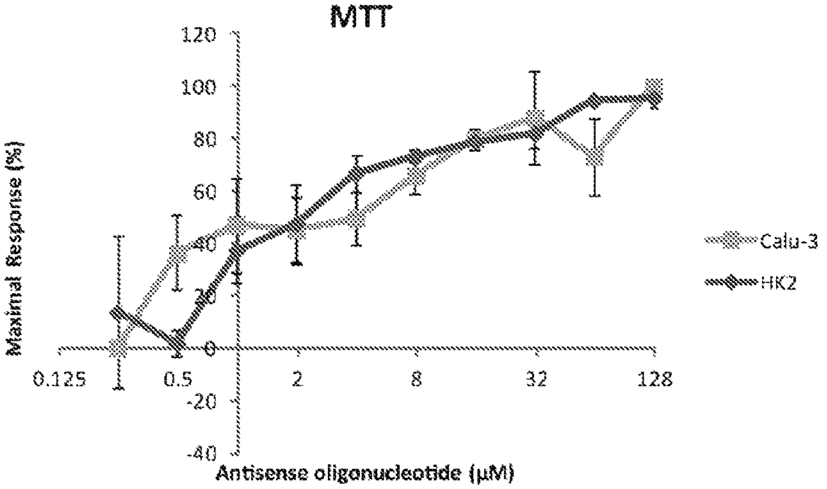
FIG. 3E shows the results of cytotoxicity studies performed using the Smad7 antisense oligonucleotides of FIGS. 3C and 3D.

FIGS. 3A to 3E show typical results of studies which demonstrate that suppression of FGF2 and Smad7 expression can subvert MERS-CoV-induced apoptosis. FIG. 3A shows the results of siRNA knockdown studies. MERS-CoV-induced Smad7 expression in HK2 cells was dampened by transfection of siRNAs (siSmad7-1, lane 1 and siSmad7-2, lane 2). Silencing siSmad7-1 pair included the sequences GUUCAGGACCAAACGAUCUGC (SEQ ID NO. 5) and GCAGAUCGUUUGGUCCUGAACAU (SEQ ID NO. 6). Silencing siRNA pair siSmad7-2 included the sequences CUCACGCACUCGGUGCUCAAG (SEQ ID NO. 7) and CUUGAGCACCGAGUGCGUGAGCG (SEQ ID NO. 8). A control siRNA (sicontrol)-transfected (lane 3) and mock-infected cells (lane 4) were also analyzed. The top left panel shows protein expression of Smad7. Gamma-tubulin was utilized as a loading control. The bottom left panel of FIG. 3A shows the mRNA levels of Smad7 normalized to those of GAPDH. Expressions (top right panel of FIG. 3A) and activities (bottom right panel of FIG. 3A) of caspase-3 were also determined. FIG. 3B shows the results of FGF2 inhibition by a small-molecule compound or antibodies. Caspase-3 activity in MERS-CoV-infected HK2 cells was measured when FGF2 signaling was blocked with a small-molecule inhibitor (for example, AG1296) (left panel, lane 1). A similar compound AG490 specifically blocking epidermal growth factor but not FGF2 signaling served as a control (left panel, lane 2). In addition, caspase-3 expressions were determined in MERS-CoV-infected HK2 cells treated with anti-FGF2 neutralizing antibodies (right panel, lane 1) or irrelevant IgG (right panel, lane 2). Mock-infected cells were also assessed (right panel, lane 3). Gamma-tubulin was utilized as a loading control. FIG. 3D shows the results of studies in which the antiviral activity of anti-Smad7 oligonucleotide was assessed by measuring the levels of viral transcript in MERS-CoV-infected HK2 (grey square) and Calu-3 cells (dark diamond). FIG. 3D shows the results of studies in which the antiviral activity of anti-Smad7 oligonucleotide was assessed by measuring the levels of virus production in MERS-CoV-infected HK2 cells (grey square) and Calu-3 cells (dark diamond). FIG. 3E shows the results of cytotoxicity studies of anti-Smad7 oligonucleotide in MERS-CoV-induced HK2 (grey square) and Calu-3 (dark diamond) cells, which was measured an MTT colorimetric assay for cellular metabolic activity.

In some embodiments of the inventive concept, modification of the expression of FGF2, Smad7, and/or sequences upstream from FGF2 can be used to prevent, reduce, or eliminate kidney and/or lung damage resulting from MERS-CoV infection, for example by reducing MERS-CoV induced apoptosis. The impact of modifying Smad7 expression on MERS-CoV-induced apoptosis can be determined by characterizing expression of activity of an apoptosis marker, such as caspase-3. For example, as shown in the left panel of FIG. 3A, application of siRNAs directed to Smad7 (e.g. siSmad7-1 and siSmad7-2) are effective in reducing Smad7 expression. As shown in the right panel of FIG. 3A application of siRNAs directed to Smad7 are also effective in reducing the expression of the apoptosis marker caspase 3 in MERS-CoV infected cells, reducing expression to levels similar to those found in mock infected cells.

In other embodiments, small molecules that can impact expression and/or activity of Smad7 and/or FGF2 (such as tyrphostin AG1296 and/or NSC37204) can be utilized to prevent, reduce, and/or eliminate apoptosis-inducing effects of MERS-CoV infection. The left panel of FIG. 3B shows typical results of the administration of a small-molecule inhibitor tyrphostin AG1296, which specifically blocks tyrosine kinase activity of the FGF receptor and hence blocks downstream signaling of FGF2 expression, on MERS-CoV-induced apoptosis in infected cells. Blockage of the downstream signaling of FGF2 reduced MERS-CoV-induced apoptosis by around 40% ($p<0.05$). Treatment with a control inhibitor tyrphostin AG490, which inhibits epidermal growth factor receptor, failed to significantly reduce MERS-CoV-induced apoptosis.

In still other embodiments a large molecule inhibitor and/or sequestering agent (for example a specific antibody or aptamer) directed to FGF2, Smad7, or a molecule expressed upstream from FGF2 can be used to prevent, reduce, and/or eliminate damage to kidney or lung tissue associated with MERS-CoV infection. As shown in the right panel of FIG. 3B, sequestration of secreted FGF2 using anti-FGF2 neutralizing antibodies can be used to reduce the functionality of expressed FGF2 in MERS-CoV infections. Addition of anti-FGF2 diminished caspase-3 expression by about 50%. Antibodies of the inventive concept can be polyclonal or monoclonal antibodies of human or animal (including avian) origin, humanized antibodies, antibody fragments, and/or single chain antibodies.

Overall, in some embodiments of the inventive concept apoptic events in kidney and/or lung tissue resulting from MERS-CoV infection can be prevented, reduced, and/or eliminated by reducing the expression or functionality of FGF2, Smad7, and or products expressed upstream from FGF2. Such reduction in expression of activity can be accomplished by genetic means (e.g. use of siRNA, antisense, and/or other oligonucleotides), small molecules (e.g. low molecular weight inhibitory compounds), and/or sequestration and/or inhibition by large molecules (such as antibodies). The effectiveness of different approaches to reduction in active FGF2, Smad7, and sequences upstream of FGF2, where such approaches are directed at different levels of achieving such activity, is indicative of this being a general phenomena that is not limited to a specific class of molecules and/or mechanism of action.

In another embodiment of the inventive concept, reduction of FGF2 and/or Smad7 expression or functionality can be utilized to reduce replication and/or spread of MERS-CoV virus. It should be appreciated that, in addition to resulting in the immediate problem of kidney and/or lung damage, MERS-CoV promotion of apoptosis in infected cells can serve to spread virus progeny to neighboring cells. In some embodiments of the inventive concept disruption of the apoptosis process induced by MERS-CoV infection (as detailed above) can also serve to interrupt the highly lytic MERS-CoV replication cycle, thereby reducing or halting the spread of the virus to adjacent, uninfected cells. For example, treatment of HK2 and Calu-3 cells with an anti-Smad7 oligonucleotide (such as GTCGCCCCTTCTCCCCGCAG (SEQ ID NO. 9)) before challenging with MERS-CoV provides a dose-dependent reduction in apoptosis. An MTT assay shows that anti-Smad7 oligo protected 50% of cells from MERS-CoV-induced apoptosis at a concentration of 0.432 μg/ml and 0.965 μg/ml in HK2 and Calu-3 cells, respectively (see FIG. 3E). In some embodiments of the inventive concept such antisense oligonucleotides can include non-natural bases and/or oligonucleotides backbone structures. For example, antisense oligonucleotides such as those represented by SEQ ID NO. 9 can substitute 5-methyl-deoxycytosine for cytosine at specific positions (for example, where C precedes G). Similarly, all or part of the phosphate backbone structure can be replaced with a non-naturally occurring structure such as O,O'-linked phosphorothioate. In some embodiments both of such alterations to the antisense sequence can be incorporated. Coincident with this, RT-qPCR quantification demonstrates that MERS-CoV virus production is inversely proportional to the concentration of the administrated anti-Smad7 oligo (see FIG. 3C). Similar results are obtained using plaque assays, which measure the amount of viable, infectious virus. In anti-Smad7 oligo-treated Calu-3 and HK2 cells, the inventors typically observed at least a 2-log reduction in virus production (see FIG. 3D) in treated cells relative to untreated cells. The highly protective effect of anti-Smad7 oligo against MERS-CoV-induced apoptosis indicates that reduction of Smad expression is a potential treatment option for MERS infection. Although the use of antisense Smad7 oligonucleotide is described, it is contemplated that antisense oligonucleotides directed to FGF2 and sequences upstream from FGF2 provide similar protection. In addition, although antisense oligonucleotides are described, the use of other inhibitory oligonucleotides (e.g. siRNA), small molecule inhibitors, and/or large molecule inhibitors and/or sequestering agents directed towards reducing the expression and/or activity of FGF2, Smad7, and/or sequences encoded upstream from FGF2 are considered. Notably, similar effects are found in both kidney and lung cells. Therefore, all considerations and advantages contemplated for kidney cells are also applicable for lung cell damage where the lungs are infected with the MERS-CoV virus.

Correlation between such in vitro studies and actual MERS infection have been confirmed using a non-human primate animal model that recapitulates the severe and sometimes lethal respiratory symptoms with disseminated extra-pulmonary infection seen in MERS-infected patients and closely resembles the clinical profile of human patients. In a typical study a group of 6 common marmosets was challenged with MERS-CoV. All MERS-CoV-inoculated common marmosets developed acute respiratory distress syndrome (ARDS), with one death due to severe illness. MER-CoV infection was confirmed by the detection of viral RNA and antigen in all lung samples collected from MERS-CoV-inoculated common marmosets (FIG. 4A, top panel, and FIG. 4B). Consistent with the clinical findings, MERS-CoV could be detected in both the upper (ULL) and lower respiratory tracts (LRL and LLL). Histopathological examination of lung biopsies revealed extensive bronchointerstitial pneumonia in severely infected common marmosets (FIG. 4C, right panels, and FIG. 4D). Results confirmed a good correlation between the amount of MERS-CoV RNA and the expression level of Smad7 and FGF2 (FIG. 4A, middle and bottom panels). Such findings are in accordance with ex vivo human organ culture and cell line data in which MERS-CoV has found to mediate apoptosis through the induction of FGF2 and Smad7.

Figure 4E:
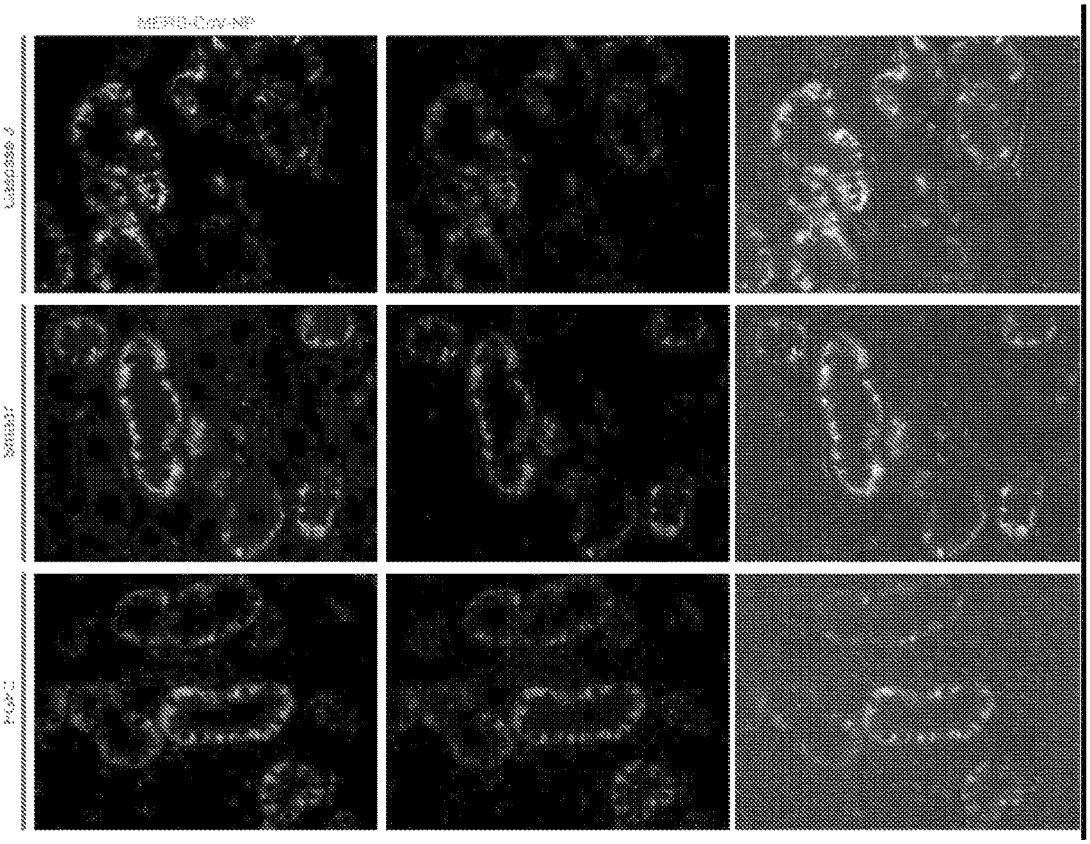
FIG. 4E shows the results of immunohistochemistry studies of kidney tissue obtained from a MERS-CoV infected animal model of human infection. Tissues were visualized using antibodies directed to caspase 3, FGF2, and Samd7.
Figure 4F:
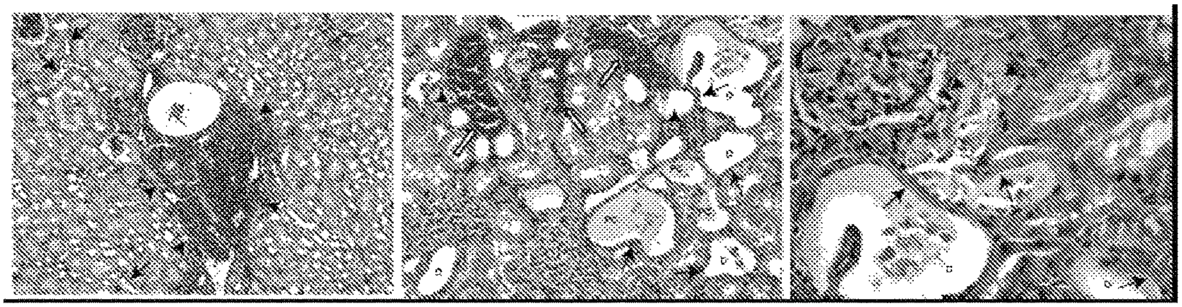
FIG. 4F shows histopathology studies of hematoxylin and eosin staining of kidney sections of a MERS-CoV infected animal model of human infection, showing characteristics of acute kidney damage.
Figure 4A:
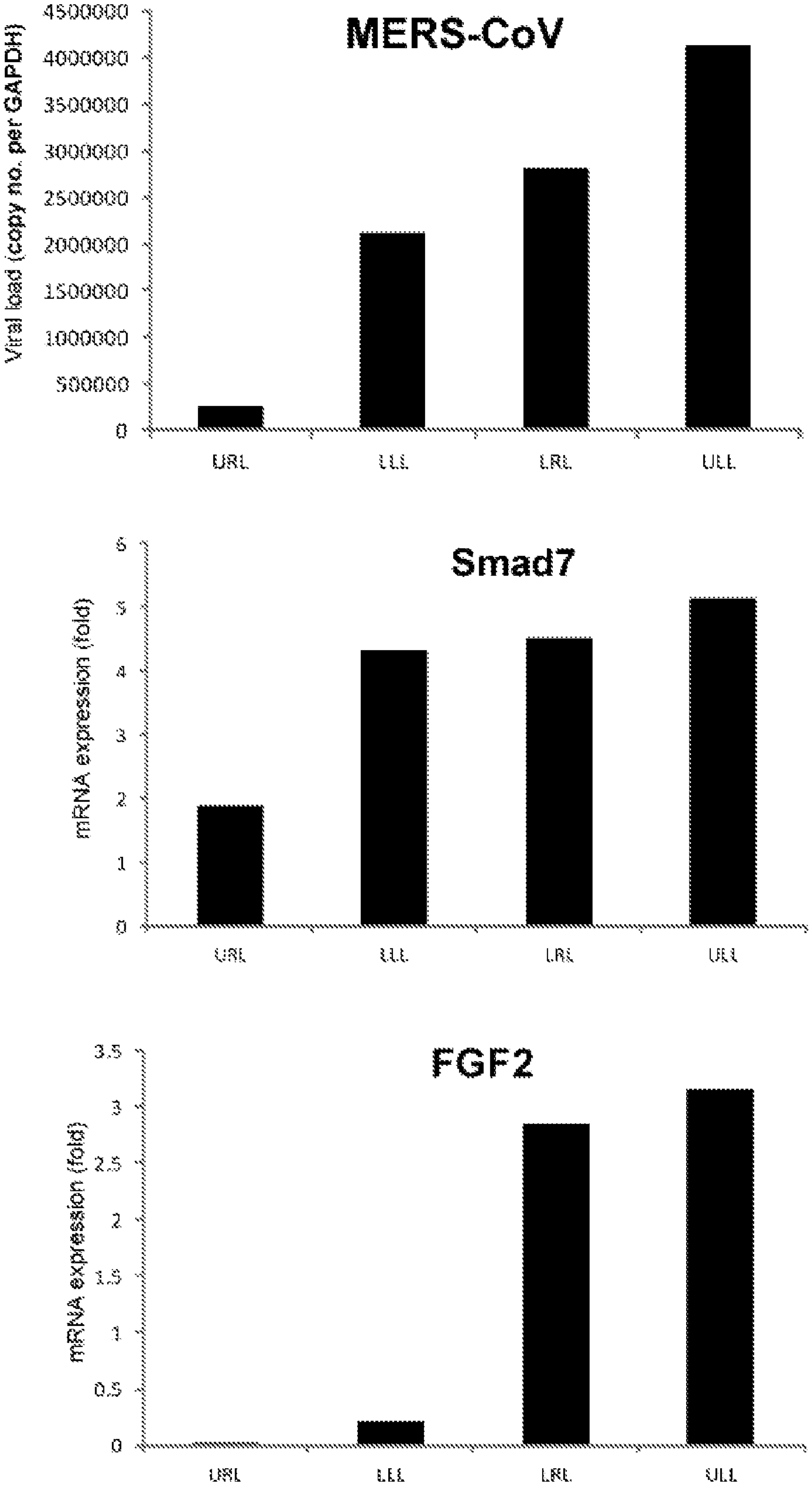
FIG. 4A shows the results of mRNA expression studies of tissue biopsies from an animal model of human MERS-CoV infection.
Figure 4B:
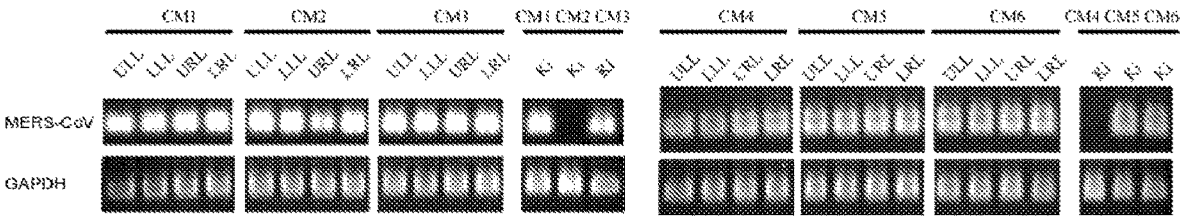
FIG. 4B shows the results of MERS-CoV RNA characterization of lung (ULL=upper left lung, LLL=lower left lung, URL=upper right lung, LRL=lower right lung) and kidney (ki) tissue samples of 6 animal subjects infected with MERS-CoV.
Figure 4C:
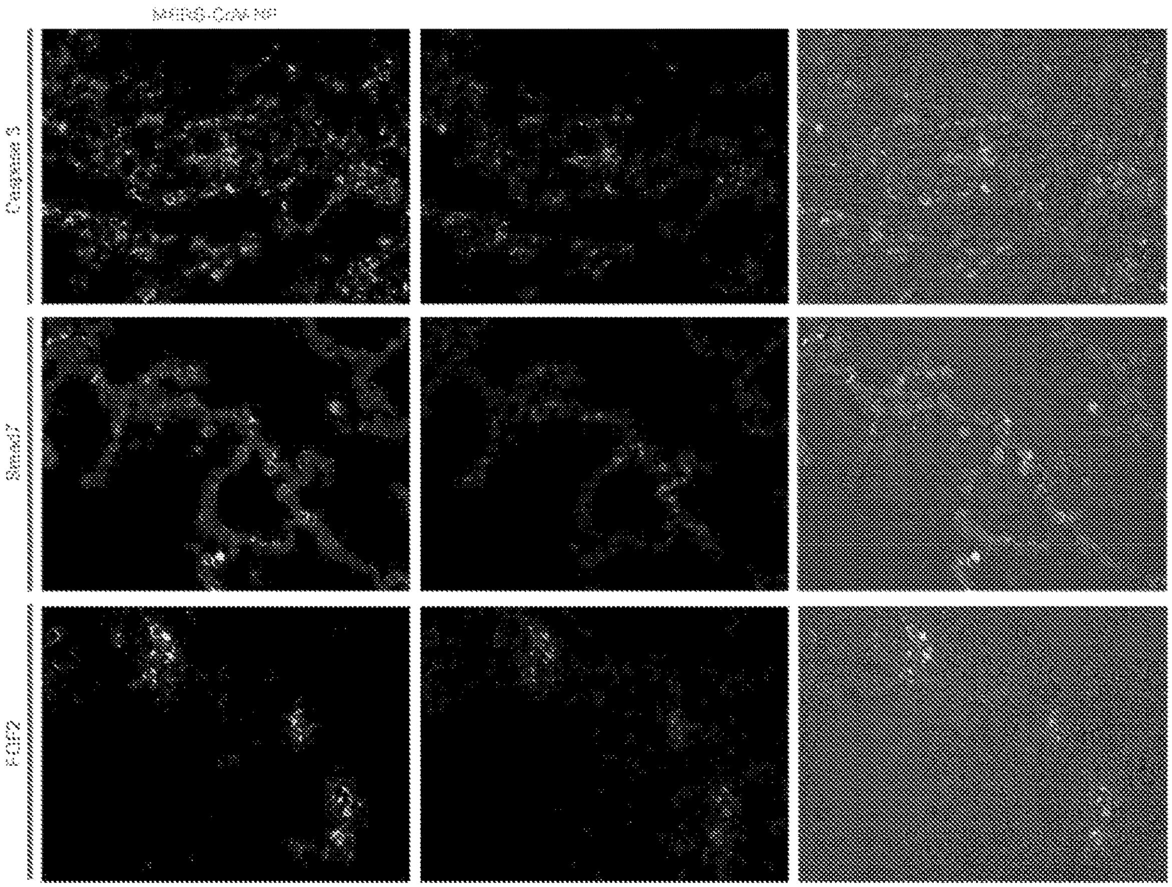
FIG. 4C shows the results of immunohistochemistry studies of lung tissue obtained from a MERS-CoV infected animal model of human infection. Tissues were visualized using antibodies directed to caspase 3, FGF2, and Samd7.
Figure 4D:
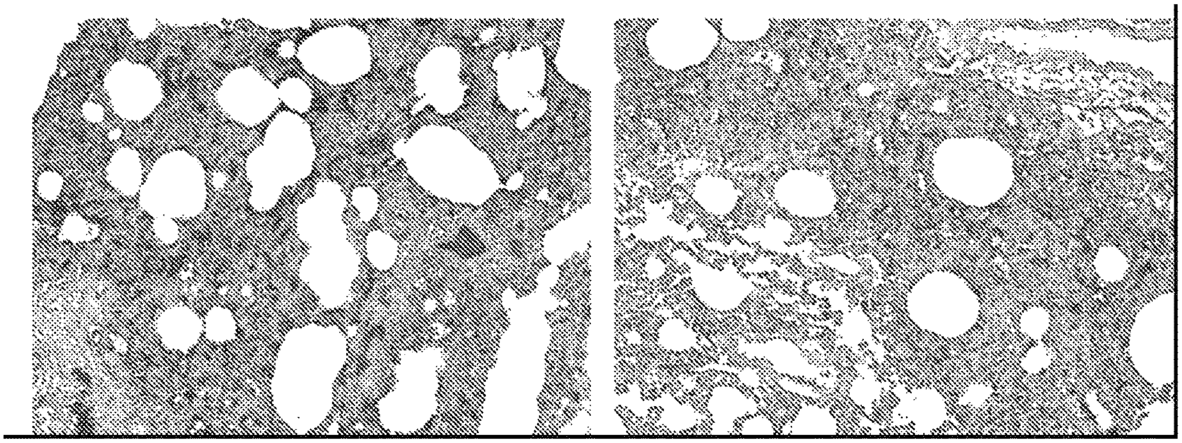
FIG. 4D shows histopathology studies of lung tissue from a MERS-CoV infected animal model of human infection, showing characteristic indications of pneumonia.

In more detail, FIGS. 4A, 4E, and 4F show the results of studies of viral loads and host gene expression in common marmosets inoculated with MERS-CoV. FIG. 4A shows the results of quantitative measurement of MERS-CoV RNA in various parts of the lungs of MERS-CoV-inoculated common marmosets (top). The relative expression levels of FGF2 (middle) and Smad7 (bottom) were indicated. All values were normalized with GAPDH. URL=upper right lung; LLL=lower left lung; LRL=lower right lung and ULL=upper left lung. FIG. 4E shows the results of co-immunohistochemical staining of MERS-CoV NP and caspase-3 (top), Smad7 (middle) and FGF2 (bottom) in kidneys of MERS-CoV-inoculated common marmosets. FIG. 4F shows the results of hematoxylin and eosin staining of kidney sections of MERS-CoV-inoculated common marmosets. Interstitial infiltration was observed in the infected kidneys (arrow heads). Characteristic clinical features of acute kidney injury, including flattened epithelial cells (arrows) and peritubular capillary congestion (white arrows), were detected in the kidney sections of MERS-CoV-inoculated common marmosets. D=dilated renal tubules; PC=protein cast.

FIGS. 4B, 4C, and 4D show the detection of MERS-CoV RNA and antigen from the lungs and kidneys of MERS-CoV-inoculated common marmosets. FIG. 4A shows the results of RT-PCR characterization of MERS-CoV RNA from different parts of lung and kidneys of the MERS-CoV-inoculated common marmosets (CM1 to CM6). URL=upper right lung; LLL=lower left lung; LRL=lower right lung; ULL=upper left lung and Ki=kidney. FIG. 4C shows the results of immunohistochemical staining of lungs from MERS-CoV-inoculated common marmosets for MERS- CoV NP, caspase-3 (top), Smad7 (middle) and FGF2 (bottom) were shown as described in FIG. 4A. FIG. 4D depicts histopathological changes in lungs of MERS-CoV-inoculated common marmosets. Infected lung tissues showed acute bronchointerstitial pneumonia with influx of inflammatory cells and thickening of alveolar septa.

Notably, in such studies viral RNA and antigen were also detected in 4 of 6 kidney samples (FIG. 4C and FIG. 4E). Intriguingly, the infected kidney samples displayed characteristic clinical features of acute kidney injury (AKI) (FIG. 4F). Identification of MERS-CoV RNA and antigens in kidney samples indicates that MERS-CoV can incur direct damage to the infected kidneys via apoptosis in vivo. Notably, co-localization of MERS-CoV NP with caspase-3, FGF2, and Smad7 was found in both renal tubular cells and lung cells. This is consistent with the Inventor's cellular infection model in which MERS-CoV induces direct cytopathic effect through the induction of apoptosis mediated through the induction of FGF2 and Smad7. Taken together, the in vitro, ex vivo and in vivo results are consistent with the Inventor's findings that Smad7 and FGF2 play important and/or central roles in MERS-induced lung and renal pathogenesis.

As noted above, in some embodiments of the inventive concept characterization of Smad7 and/or FGF2 expression can be utilized to diagnose renal disease associated with MERS-CoV infection. In such an embodiment expression can be characterized in terms of nucleotide expression and/or protein expression. Nucleotide expression (e.g. mRNA expression) of Smad7 and/or FGF2 can be performed by any suitable technique, including RT-PCR, real time RT-PCR, and direct hybridization. Protein expression (e.g. detection of intra- or extra-cellular Smad7 and/or FGF2) can be performed by any suitable method, including immunological assays (such as EIA, RIA, and/or FIA), immunofluorescent staining, FACS, and so on. Such protein expression techniques can be applied to any suitable sample, such as whole blood, plasma, serum, saliva, lacrimal fluid, synovial fluid, mucus, interstitial fluids, and/or tissue samples. Results of such nucleotide and/or protein expression studies can be quantitative or non-quantitative, and in some embodiments can be performed on an automated system.

In other embodiments of the inventive concept characterization of Smad7 and/or FGF2 expression is utilized in a prognostic fashion to characterize a stage of renal disease associated with MERS-CoV infection or to provide a clinician with insight into the probable course of such disease. In such an embodiment expression can be characterized in terms of nucleotide expression and/or protein expression. Nucleotide expression (e.g. mRNA expression) of Smad7 and/or FGF2 can be performed by any suitable technique, including RT-PCR, real time RT-PCR, and direct hybridization. Protein expression (e.g. detection of intra- or extra-cellular Smad7 and/or FGF2) can be performed by any suitable method, including immunological assays (such as EIA, RIA, and/or FIA), immunofluorescent staining, FACS, and so on. S Such protein expression techniques can be applied to any suitable sample, such as whole blood, plasma, serum, saliva, lacrimal fluid, synovial fluid, mucus, interstitial fluids, and/or tissue samples Results of such nucleotide and/or protein expression studies can be quantitative or non-quantitative, and in some embodiments can be performed on an automated system.

In another embodiment of the inventive concept, methods and compositions that reduce the expression and/or the effective expression of FGF2, Smad7, and/or sequences that are upstream of FGF2 are used to reduce or eliminate renal failure resulting from MERS-CoV infection. In some embodiments this reduction in expression is accomplished at the transcription level, for example by treatment with siRNA, RNAi, and antisense polynucleotides that interfere with effective transcription and/or translation of FGF2, Smad7, and/or a sequence upstream from FGF2. In other embodiments of the inventive concept peptides, proteins, and/or small (i.e. less than about 500 D) molecule that interact with regulatory regions associated with FGF2, Smad7, and/or sequences upstream from FGD2 are used to inhibit or reduce transcription of these sequences.

In still further contemplated aspects of the inventive subject matter, the inventors also contemplate that drugs that inhibit or reduce apoptosis can be used (alone or in combination with the treatment modalities presented herein) to reduce or abrogate lung and/or kidney cell damage for MERS infected cells. For example, contemplated drugs include Kaletra™ (a combination of lopinavir/ritonavir) or other drugs with anti-apoptotic effects including antioxidants, cell cycle inhibitors, BAX inhibitors, caspase-3 inhibitors, PARP inhibitors, or GSK3β inhibitors.

In other embodiments of the inventive concept, renal disease associated with MERS-CoV infection can be reduced or eliminated by effectively reducing the expression of FGF2, Smad7, and or a sequence upstream of FGF2 by reducing the availability of the proteins associated with these sequences. In such embodiments a binding partner with an affinity for FGF2, Smad7, or a protein product of a sequence upstream of Smad7 can be utilized to complex with, inactivate, and/or reduce the functionality of such proteins. Suitable binding partners include natural and/or synthetic antibodies, polyclonal antibodies, monoclonal antibodies, humanized antibodies, antibody fragments, single chain antibodies, and/or aptamers.

In other embodiments of the inventive concept, renal disease associated with MERS-CoV infection can be mitigated using compounds that interact with regulatory pathways associated with FGF2, Smad7, and/or sequences located upstream of FGF2. For example, proteins, peptides, and/or small molecules that block or interfere with the activity of receptors for FGF2 protein and/or Smad7 protein and subsequently result in down regulation of transcription of the related gene(s) can be used.

In contemplating such treatment modalities, it should be appreciated that there are a variety of ways in which such compounds can be administered. The compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered orally, intraperitoneally, or intravenously.

For example, sterile injectable forms of contemplated compounds may be aqueous solutions or oleaginous suspensions. These suspensions may be formulated according to techniques known in the art using suitable dispersing or wetting agents and suspending agents. A sterile injectable preparation can also be prepared as a sterile injectable solution or suspension in a non-toxic parenterally acceptable diluent or solvent, for example as a solution in 1,3-butanediol. Among other acceptable vehicles and solvents, especially contemplated liquids include water, Ringer's solution, and isotonic sodium chloride solution. In addition, sterile, fixed oils may be employed as a co-solvent or suspending medium (e.g., natural or synthetic mono- or diglycerides). Fatty acids may also be used, and suitable fatty acids include oleic acid and its glyceride derivatives, olive oil, castor oil, especially in their polyoxyethylated versions. Such oil solutions or suspensions may further contain a long-chain alcohol diluent or dispersant.

In another example, contemplated compounds may be orally administered in any orally acceptable dosage form, including capsules, tablets, aqueous suspensions, or solutions. In the case of tablets for oral use, all pharmaceutically acceptable carriers (e.g., lactose, corn starch, etc) are deemed suitable. Similarly, various lubricating agents may be added (e.g., magnesium stearate). For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Pharmaceutical compositions of the inventive concept can also be administered topically, especially when the target of treatment includes areas or organs readily accessible by topical application, including diseases of the eye, the skin, the lower intestinal tract, or areas exposed during surgical intervention. There are numerous topical formulations known in the art, and all of such formulations are deemed suitable for use herein.

For topical applications, contemplated compositions may be formulated in a suitable ointment, cream, gel, and/or suspension containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

Pharmaceutical compositions according to the inventive subject matter can also be administered by nasal aerosol or particulate inhalation. Such compositions are prepared according to techniques well-known in the art of pharmaceutical formulation and may be prepared as dry powders or as solutions in saline, employing benzyl alcohol or other suitable preservatives, absorption promoters to enhance bioavailability, fluorocarbons, and/or other conventional solubilizing or dispersing agents.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in an amount of between about 0.1 ng/ml to about 100 mg/ml, more typically in an amount of between about 10 ng/ml to about 100 mg/ml, and most typically between about 1 μg/ml to about 100 μg/ml. Where the formulation is a solid, contemplated compounds will be present in an amount of between about 0.1 ng/g to about 100 mg/g, more typically in an amount of between about 10 ng/g to about 10 mg/g, and most typically between about 1 μg/g to about 100 μg/g. With respect to a dosage unit, it is generally contemplated that contemplated compounds are administered at a dosage effective to achieve a desired therapeutic effect in vitro and/or in vivo.

Therefore, suitable amounts of contemplated compounds will be in the range of 0.1 μg per dosage unit to about 0.5 gram per dosage unit, more typically between 10 μg per dosage unit to about 0.05 gram per dosage unit, and most typically between 50 μg per dosage unit to about 100 mg per dosage unit. Thus, suitable dosages will be in the range of about 0.01 μg/kg and 100 mg/kg, more typically between 1 μg/kg and 50 mg/kg, and most typically between 10 μg/kg and 10 mg/kg.

EXAMPLES

Viruses:

SARS-CoV strain HKU39849 and MERS-CoV isolate HCoV-EMC/2012 were provided by Ron Fouchier[27]. Viruses were propagated in VeroE6 cells (obtained from ATCC) in Dulbecco modified Eagle Medium (DMEM) supplemented with 10% fetal calf serum (FCS) and 100 units/ml penicillin+100 μg/ml streptomycin (1% PS). All studies were performed according to biosafety level 3 practices.

Virus Titration by $TCID_{50}$ Assay:

The 50% tissue culture infectious dose ($TCID_{50}$) per ml was determined for MERS-CoV and SARS-CoV in VeroE6 cells by observation of cytopathic effects (CPE). Briefly, cells were plated in 96-well plates at a density of $5\times10^4$ cells/well in 150 μl of DMEM. The virus was serially diluted by half-log from $10^3$ to $10^{14}$ in DMEM. One hundred microliters of each dilution was added per well; and the plates were observed daily for CPE for 5 consecutive days.

Cell Culture:

HK-2 cells (obtained from ATCC) were cultured in DMEM/F12 medium (obtained from Life Technologies) supplemented with 5% FCS and 1% PS. Normal Human Mesangial cells (NHMC) (obtained from Lonza) were cultured in Mesangial Cell Basal Medium (MsBM) (obtained from Lonza) supplemented with 10% FCS, 1% PS, 5 μg/ml transferrin and 5 μg/ml insulin. All experiments using NHMC were done within their tenth passage.

Ex Vivo Human Kidney and Lung Organ Culture and Infection:

Fresh surgically resected kidney or lung specimens were obtained from patients undergoing nephrectomy or pneumonectomy, respectively, at Queen Mary Hospital, Hong Kong, as part of the standard clinical management. Ex vivo cultures were performed[28]. The kidney cortical and lung tissues in small strips of 1 mm width were placed into a 24-well plate directly with 1 ml of Kaighn's Modification of Ham's F-12 Medium (F-12K) and with 1% PS at 37° C. Tissues were infected with MERS-CoV and SARS-CoV at a viral titer of 6 logs $TCID_{50}$ s/ml for 4 hours at 37° C. Unbound viruses were washed away with phosphate buffered saline (PBS). Tissues were collected at 0, 18, 48, and 72 hours post-infection (hpi) and then fixed in 10% paraformaldehyde for immunohistochemistry and electron microscopy.

Common Marmoset Infection Model:

The experiments were performed as the inventors and others have described previously[25,26] with modifications. Briefly, six male common marmosets (*Callithrix jacchus;* 3 years old) were inoculated with MERS-CoV intranasally with 100 μl in each nare, 500 μl orally, 500 μl intratracheally, and 50 μl in each eye with DMEM containing a total dose of $1\times10^7$ $TCID_{50}$ of MERS-CoV. Necropsies of the six common marmosets were scheduled on 3 days post-infection (dpi). The common marmosets were observed twice daily for clinical signs of disease and scored using a clinical scoring system prepared for common marmosets[26]. The in-study euthanasia criteria were established prior to the start of the experiment based on the scoring sheet and euthanasia was indicated at a clinical score of 35 or above. On 1 and 3 dpi, clinical examinations were performed on anaesthetized animals, X-rays were taken and nasal, oral, and rectal swabs were collected in 1 ml DMEM with 50 U/ml penicillin and 50 mg/ml streptomycin. Samples of all lung lobes, kidney, heart, liver, spleen, brain, lymph node, salivary gland, pancreas, adrenal gland, bladder and spleen were collected on necropsy.

Figure 5:
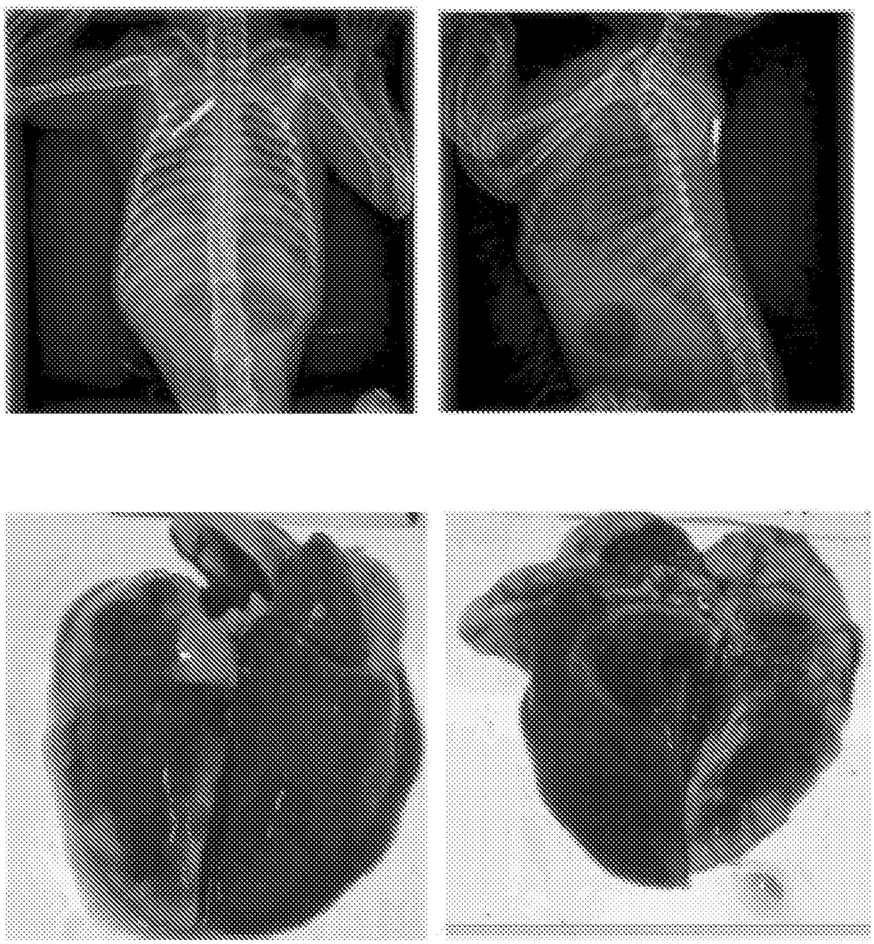
FIG. 5 shows the results of MERS-CoV infection on the lungs of MERS-CoV infected animal models. The upper panels of FIG. 5 show radiographic studies of lung pathology following MERS-CoV infection. Lower panels of FIG. 5 depict gross pathology of necropsied lungs from the animals shown in the upper panels.

Results of these studies are shown in FIG. 5. The upper panels of FIG. 5 show the results of radiographic studies demonstrating radiographic alterations and photographs of lung pathology following MERS-CoV infection. Specifically, the upper panels of FIG. 5 depict dorsal-ventral and lateral thoracic X-rays from MERS-CoV-inoculated common marmosets at 3 days post-inoculation. The lower panels of FIG. 5 depict the gross pathology of the necropsied lungs from the animals shown in the upper panels. Changes associated with damage to pulmonary tissue are evident.

Immunohistochemical Staining and Electron Microscopy:

Infected primate kidneys were fixed in 10% paraformaldehyde and cryosectioned. The mounted slides were blocked with TBS4 for 1 hour. MERS-CoV NP was stained with mouse anti-MERS-CoV NP (1:200) overnight at 4° C. Rabbit antibodies against cell type-specific markers synaptopodin (obtained from Abcam), CD31 (obtained from Abcam), cytokeratin 18 (obtained from Abcam), Smad7 (obtained from Santa Cruz), FGF2 (obtained from Abcam) and Caspase-3 (obtained from Cell Signaling Technology) were also used. Unbound antibodies were washed away with 3× phosphate buffered saline (PBS) with Tween-20 (PBST). Alexa Fluor 488 goat anti-mouse IgG (H+L) antibodies (1:500) (Life Technologies) and Alexa Fluor 594 goat anti-rabbit IgG (1:500) (obtained from Life Technologies) was then applied to the slides for signal detection, followed by washing with 3×PBST. Stained slides were then mounted with coverslips in the presence of anti-fade mountant (obtained from Dako) and 1 μg/ml DAPI (obtained from Sigma). Human kidney tissues were embedded in Tissue-Tek OCT compound (obtained from Miles Inc., Elkhart, Ind.), snap frozen and stored at −80° C. before sectioning. Sections of 5-10 μm thickness were cut on a cryostat and transferred to glass microscope slides pre-coated with poly-lysine (obtained from Sigma-Aldrich). Sections were then fixed with cold acetone for 20 minutes at room temperature. Fixed sections were washed three times with PBS before blocking and staining with anti-MERS-CoV NP as described above. Digital images were acquired using NIKON Eclipse Ni-U with SPOT RT3 camera. To prepare samples for electron microscopic examination, the paraformaldehyde fixed tissues were post-fixed for 30 minutes with 0.5% osmium tetroxide/0.8% potassium ferricyanide in 0.1 M sodium cacodylate, 1 hour with 1% tannic acid and overnight with 1% uranyl acetate at 4° C. Specimens were dehydrated with a graded ethanol series from water through 10%-20%-50%-95%-100% ethanol with two final exchanges in 100% propylene oxide before infiltration and final embedding in Embed-812® resin. Thin sections were cut with a Leica EM UC6 ultra microtome (obtained from Leica), and stained with 1% uranyl acetate and Reynold's lead citrate before viewing at 120 kV on a FEI Tecnai G2 20 S-TWIN Scanning Transmission Electron Microscope. Digital images were acquired with a Gatan 794 1K×1K Camera System with DigitalMicrograph Acquisition Software.

Quantitative Real-Time PCR (qPCR):

Total RNAs and viral RNAs were isolated using Trizol® (obtained from Life Technologies Ltd.) and Viral RNA Mini kit (obtained from QIAGEN), respectively. After RNA quantification, 1 μg of RNAs was reverse transcribed into cDNA using random hexamers. Total MERS-CoV transcripts were detected using Novel Coronavirus 2012 Real-Time RT-PCR assay (obtained from CDC; Catalog # KT0136). The viral RNAs isolated from cell lysates and conditioned media were normalized with the mRNA expression level of GAPDH and a spike-in control, enterovirus 71 (EV71) strain SZ/HK08-5, using primers 5'-GCTCACTGGCATGGCCTTCCGTGT-3' (GADPH, SEQ ID NO. 1) and 5'-TGGAGGAGTGGGT-GTCGCTG TTGA-3' (GAPDH, SEQ ID NO. 2) as well as 5'-CCCCTGAATGCGGCTAATCC-3' (EV71, SEQ ID NO. 3) and 5'-ACACGGACACCCAAAGTAGT-3' (EV71, SEQ ID NO. 4). For each reaction, equal amounts of cDNA were mixed with FS Universal SYBR Green Master Rox® (obtained from Roche) plus 5 pmol each of forward and reverse primers. Amplification was done under thermal cycling conditions of 15 seconds at 95° C. and 1 minute at 60° C. for 55 cycles in a 7900 real-time PCR detection System® (obtained from ABI).

High-Throughput Sequencing:

Sequencing libraries were prepared at the Centre for Genomic Sciences, the University of Hong Kong by using the TruSeq Stranded mRNA Sample Prep Kit® (obtained from Illumina), and were subsequently sequenced on a Illumina HiSeq 2000® system. Briefly, mRNA was isolated using polyT oligo-attached magnetic beads. The purified mRNA was fragmented and reverse transcribed using SuperScript II® Reverse Transcriptase (obtained from Invitrogen) to first-strand cDNA in the presence of random hexamers. Double-stranded cDNAs were synthesized by second strand synthesis and then subjected to end repair, 3' adenylation and indexed adaptor ligation. The adaptor-ligated sequencing libraries were further enriched by 10 cycles of PCR, quantified and sequenced on a HiSeq 2000® system with 101 bp paired-end reads. Image analyses and base calling were performed with SCS2.8/RTA1.8® software (obtained from Illumina). FASTQ file generation and the removal of failed reads were performed using CASAVA® ver.1.8.2 software (obtained from Illumina).

Apoptosis Assay:

A caspase-3/CPP32 fluorometric assay kit (obtained from BioVision) was used for measurement of caspase-3 activity. Briefly, cells were plated in six-well dishes, cultured, collected, and lysed in lysis buffer at 0, 8, 48 and 72 hpi. After the protein concentration was normalized by a Bradford protein assay. The lysates were incubated with the same amounts of reaction buffer and 50 mmol/L of DEVD-AFC substrate for 2 hours at 37° C. Fluorescence was monitored with an excitation wavelength of 400 nm and an emission wavelength of 505 nm.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

REFERENCES

1. Peiris, J. S., et al. Coronavirus as a possible cause of severe acute respiratory syndrome. *Lancet* 361, 1319-1325 (2003).
2. Peiris, J. S., Guan, Y. & Yuen, K. Y. Severe acute respiratory syndrome. *Nature medicine* 10, S88-97 (2004).
3. Cheng, V. C., Lau, S. K., Woo, P. C. & Yuen, K. Y. Severe acute respiratory syndrome coronavirus as an agent of emerging and reemerging infection. *Clin Microbiol Rev* 20, 660-694 (2007).
4. Eckerle, I., Muller, M. A., Kallies, S., Gotthardt, D. N. & Drosten, C. In-vitro renal epithelial cell infection reveals a viral kidney tropism as a potential mechanism for acute renal failure during Middle East Respiratory Syndrome (MERS) Coronavirus infection. *Virol J* 10, 359 (2013).
5. Chan, J. F., et al. Differential cell line susceptibility to the emerging novel human betacoronavirus 2c EMC/2012: implications for disease pathogenesis and clinical manifestation. *J Infect Dis* 207, 1743-1752 (2013).
6. Chan, J. F., et al. Is the discovery of the novel human betacoronavirus 2c EMC/2012 (HCoV-EMC) the beginning of another SARS-like pandemic? *J Infect* 65, 477-489 (2012).
7. Chan, J. F., Lau, S. K. & Woo, P. C. The emerging novel Middle East respiratory syndrome coronavirus: the "knowns" and "unknowns". *J Formos Med Assoc* 112, 372-381 (2013).
8. Eckerle, I., Muller, M. A., Kallies, S., Gotthardt, D. N. & Drosten, C. In-vitro renal epithelial cell infection reveals a viral kidney tropism as a potential mechanism for acute renal failure during Middle East Respiratory Syndrome (MERS) Coronavirus infection. *Virology journal* 10, 359 (2013).
9. Assiri, A., et al. Epidemiological, demographic, and clinical characteristics of 47 cases of Middle East respiratory syndrome coronavirus disease from Saudi Arabia: a descriptive study. *The Lancet infectious diseases* 13, 752-761 (2013).
10. Hung, I. F., et al. Viral loads in clinical specimens and SARS manifestations. *Emerging infectious diseases* 10, 1550-1557 (2004).
11. Lu, L., Liu, Q., Zhu, Y., Chan, K. H., Qin, L., Li, Y., Wang, Q., Chan, J. F., Du, L., Yu, F., Ma, C., Ye, S., Yuen, K. Y., Zhang, R., Jiang, S. Structure-based discovery of Middle East respiratory syndrome coronavirus fusion inhibitor. *Nature Communications* (2014).
12. Chan, J. F., et al. Broad-spectrum antivirals for the emerging Middle East respiratory syndrome coronavirus. *The Journal of infection* 67, 606-616 (2013).
13. Falzarano, D., et al. Inhibition of novel beta coronavirus replication by a combination of interferon-alpha2b and ribavirin. *Scientific reports* 3, 1686 (2013).
14. Al-Tawfiq, J. A., Momattin, H., Dib, J. & Memish, Z. A. Ribavirin and interferon therapy in patients infected with the Middle East respiratory syndrome coronavirus: an observational study. *International journal of infectious diseases: IJID: official publication of the International Society for Infectious Diseases* (2014).
15. Chan, K. H., et al. Cross-reactive antibodies in convalescent SARS patients' sera against the emerging novel human coronavirus EMC (2012) by both immunofluorescent and neutralizing antibody tests. *The Journal of infection* 67, 130-140 (2013).
16. Drosten, C., et al. Clinical features and virological analysis of a case of Middle East respiratory syndrome coronavirus infection. *Lancet Infect Dis* 13, 745-751 (2013).
17. Schiffer, M., et al. Apoptosis in podocytes induced by TGF-beta and Smad7. *J Clin Invest* 108, 807-816 (2001).
18. Lan, H. Y., et al. Inhibition of renal fibrosis by gene transfer of inducible Smad7 using ultrasound-microbubble system in rat UUO model. *J Am Soc Nephrol* 14, 1535-1548 (2003).
19. Okado, T., et al. Smad7 mediates transforming growth factor-beta-induced apoptosis in mesangial cells. *Kidney international* 62, 1178-1186 (2002).
20. Bitzer, M., et al. A mechanism of suppression of TGF-beta/SMAD signaling by NF-kappa B/RelA. *Genes Dev* 14, 187-197 (2000).
21. Floege, J., et al. Basic fibroblast growth factor augments podocyte injury and induces glomerulosclerosis in rats with experimental membranous nephropathy. *J Clin Invest* 96, 2809-2819 (1995).
22. Li, Z., Jerebtsova, M., Liu, X. H., Tang, P. & Ray, P. E. Novel cystogenic role of basic fibroblast growth factor in developing rodent kidneys. *American journal of physiology. Renal physiology* 291, F289-296 (2006).
23. Zorzi, F., et al. A phase 1 open-label trial shows that smad7 antisense oligonucleotide (GED0301) does not increase the risk of small bowel strictures in Crohn's disease. *Alimentary pharmacology & therapeutics* 36, 850-857 (2012).
24. Monteleone, G., et al. Phase I clinical trial of Smad7 knockdown using antisense oligonucleotide in patients with active Crohn's disease. *Molecular therapy: the journal of the American Society of Gene Therapy* 20, 870-876 (2012).
25. Yao, Y., et al. An animal model of MERS produced by infection of rhesus macaques with MERS coronavirus. *J Infect Dis* 209, 236-242 (2014).
26. Falzarano, D., et al. Infection with MERS-CoV causes lethal pneumonia in the common marmoset. *Plos Pathog* 10, e1004250 (2014).
27. Zaki, A. M., van Boheemen, S., Bestebroer, T. M., Osterhaus, A. D. & Fouchier, R. A. Isolation of a novel coronavirus from a man with pneumonia in Saudi Arabia. *The New England journal of medicine* 367, 1814-1820 (2012).
28. Zhou, J., et al. *Active Replication of Middle East Respiratory Syndrome Coronavirus* Replication and Aberrant Induction of Inflammatory Cytokines and Chemokines in Human Macrophages: Implications for Pathogenesis. *The Journal of infectious diseases* (2013).
29. Chan, J. F., et al. Differential cell line susceptibility to the emerging novel human betacoronavirus 2c EMC/2012: implications for disease pathogenesis and clinical manifestation. *The Journal of infectious diseases* 207, 1743-1752 (2013).

What is claimed is:

1. A method of preventing renal disease associated with MERS-CoV infection, comprising reducing bioavailability of FGF2 or Smad7 in an individual infected with MERS-CoV, wherein a reduction of bioavailability is achieved by at least one of reducing gene expression and reducing bioavailability of a product of gene expression.

2. The method of claim 1, further comprising a step of reducing expression a gene encoding for FGF2 or Smad7.

3. The method of claim 1, further comprising a step of administering a polynucleotide that interferes with transcription or translation of FGF2 or Smad7.

4. The method of claim 1, further comprising a step of administering a compound that interacts with a regulatory element that regulates transcription of FGF2 or Smad7.

5. The method of claim 1, further comprising a step of adminstering a compound that interacts with a regulatory pathway that regulates transcription of FGF2 or Smad7.

6. The method of claim 1, wherein bioavailability is reduced by administration of a binding partner with an affinity for a polypeptide corresponding to FGF2 or Smad7.

7. A method of treating renal disease associated with MERS-CoV infection, comprising reducing bioavailability of FGF2 or Smad7 in an individual infected with MERS-CoV, wherein a reduction of bioavailibility is achieved by at least one of reducing gene expression and reducing bioavailability of a product gene expression.

8. The method of claim 7, further comprising a step of reducing expression of a gene encoding FGF2 or Smad7.

9. The method of claim 7, further comprising a step of administering a polynucleotide that interferes with transcription or translation of FGF2 or Smad7.

10. The method of claim 7, further comprising a step of administering a compound that interacts with a regulatory element that regulates transcription of FGF2 or Smad7.

11. The method of claim 7, furhter comprising a step of administering a compound that interacts with a regulatory pathway that regulates transcription of FGF2 or Smad7.

12. The method of claim 7, wherein bioavailability is reeduced by administration of a binding partner with an affinity for FGF2 or Smad7.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Homo sapiens
<220> FEATURE:
<221> NAME/KEY: primer
<222> LOCATION: (1)..(24)
<223> OTHER INFORMATION: GAPDH primer

<400> SEQUENCE: 1
mgctcactgg catggccttc cgtgt 25

<210> SEQ ID NO 2
<211> LENGTH: 24
<212> TYPE: DNA
<213> ORGANISM: Homo sapiens
<220> FEATURE:
<221> NAME/KEY: primer
<222> LOCATION: (1)..(24)
<223> OTHER INFORMATION: GAPDH primer

<400> SEQUENCE: 2
tggaggagtg ggtgtcgctg ttga 24

<210> SEQ ID NO 3
<211> LENGTH: 20
<212> TYPE: DNA
<213> ORGANISM: Enterovirus 71
<220> FEATURE:
<221> NAME/KEY: primer
<222> LOCATION: (1)..(20)
<223> OTHER INFORMATION: enterovirus 71 primer

<400> SEQUENCE: 3
cccctgaatg cggctaatcc 20

<210> SEQ ID NO 4
<211> LENGTH: 20
<212> TYPE: DNA
<213> ORGANISM: Enterovirus 71
<220> FEATURE:
<221> NAME/KEY: primer
<222> LOCATION: (1)..(20)
<223> OTHER INFORMATION: enterovirus 71 primer

<400> SEQUENCE: 4
acacggacac ccaaagtagt 20

<210> SEQ ID NO 5
<211> LENGTH: 21
<212> TYPE: RNA
<213> ORGANISM: Artificial Sequence
<220> FEATURE:
<223> OTHER INFORMATION: siRNA targeting SMAD7-1 (siSmad7-1)

<400> SEQUENCE: 5
guucaggacc aaacgaucug c 21

<210> SEQ ID NO 6
<211> LENGTH: 23
<212> TYPE: RNA
<213> ORGANISM: Artificial Sequence
<220> FEATURE:
<223> OTHER INFORMATION: siRNA targeting Smad7-1 (siSmad7-1)

<400> SEQUENCE: 6

```
gcagaucguu ugguccugaa cau                                              23

<210> SEQ ID NO 7
<211> LENGTH: 21
<212> TYPE: RNA
<213> ORGANISM: Artificial Sequence
<220> FEATURE:
<223> OTHER INFORMATION: siRNA targeting Smad7-2 (siSmad7-2)

<400> SEQUENCE: 7

cucacgcacu cggugcucaa g                                                21

<210> SEQ ID NO 8
<211> LENGTH: 23
<212> TYPE: RNA
<213> ORGANISM: Artificial Sequence
<220> FEATURE:
<223> OTHER INFORMATION: siRNA targeting Smad7-2 (siSmad7-2)

<400> SEQUENCE: 8

cuugagcacc gagugcguga gcg                                              23

<210> SEQ ID NO 9
<211> LENGTH: 20
<212> TYPE: DNA
<213> ORGANISM: Artificial Sequence
<220> FEATURE:
<223> OTHER INFORMATION: antisense oligonucleotide targeting Smad7
      (anti-Smad7 oligo; GED0301)

<400> SEQUENCE: 9

gtcgcccctt ctccccgcag                                                  20

<210> SEQ ID NO 10
<211> LENGTH: 20
<212> TYPE: DNA
<213> ORGANISM: Artificial Sequence
<220> FEATURE:
<223> OTHER INFORMATION: Modified antisense oligonucleotide targeting
      SMad7: n = 5-methyl-deoxycytosine and internucleotide linkages are
      modified to O,O-linked phosphorothioates
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 10

gtngcccctt ctcccngcag                                                  20
```